(12) United States Patent
Kang et al.

(10) Patent No.: US 10,960,036 B2
(45) Date of Patent: Mar. 30, 2021

(54) **PHARMACEUTICAL COMPOSITION FOR PREVENTING AND TREATING ALPHA HERPES VIRUS INFECTION, CONTAINING, AS ACTIVE INGREDIENT, *ELAEOCARPUS SYLVESTRIS* EXTRACT OR FRACTION THEREOF**

(71) Applicant: Genencell Co., Ltd., Gyeonggi-do (KR)

(72) Inventors: Se Chan Kang, Gyeonggi-do (KR); Dae Won Park, Seoul (KR)

(73) Assignee: GENENCELL Co., Ltd., Heungdeok-Ro (KR)

( * ) Notice: Subject to any disclaimer, the term of this patent is extended or adjusted under 35 U.S.C. 154(b) by 0 days.

(21) Appl. No.: 16/796,062

(22) Filed: Feb. 20, 2020

(65) Prior Publication Data

US 2020/0261523 A1 Aug. 20, 2020

Related U.S. Application Data

(63) Continuation of application No. 16/331,876, filed as application No. PCT/KR2017/004614 on Apr. 28, 2017, now abandoned.

(30) Foreign Application Priority Data

Sep. 9, 2016 (KR) .................. 10-2016-0116611

(51) Int. Cl.
*A61K 36/185* (2006.01)
*A23L 33/105* (2016.01)
*A61P 31/22* (2006.01)
*A61K 31/235* (2006.01)
*A61K 31/365* (2006.01)

(52) U.S. Cl.
CPC .......... *A61K 36/185* (2013.01); *A23L 33/105* (2016.08); *A61K 31/235* (2013.01); *A61K 31/365* (2013.01); *A61P 31/22* (2018.01); *A23V 2002/00* (2013.01); *A61K 2236/33* (2013.01)

(58) Field of Classification Search
None
See application file for complete search history.

(56) References Cited

FOREIGN PATENT DOCUMENTS

KR 10-0791108 1/2008
KR 10-0047756 5/2015

OTHER PUBLICATIONS

ISR/KR, International Search Report for PCT/KR2017/004614 (dated Aug. 8, 2017) (2 pages).
Kane, et al., "Methyl Gallate, Methyl-3,4,5-trihydroxybenzoate, Is a potent and Highly Specific Inhibitor of herpes Simplex virus in Vitro. II. Antiviral Activity of Methyl Gallate and Its Derivatives," Bioscience Reports, 1988, vol. 8, No. 1, pp. 95-102.
Kwon et al., "Isolation of Anti-herpes Simplex Virus-1 Activity Constituents from Elaeocarpus sylvestris", Abstract, p. 258,, 2016 General Assembly Meeting and Spring Conference of the Plant Resources Society of Korea, The Plant Resources of Tropical and Sub-Tropical Zone, Apr. 28, 2016 (with English translation) (5 pages).
Prihantini, et al., "Antioxidant Active Compounds from Elaeocarpus-sylvestris and Their Relationship between Structure and Activity" Procedia Environmental Sciences, 2015, vol. 28, pp. 758-768.
To, et al., "The Extract of elaeocarpus Sylvestris Inhibits Human Cytomegalovirus Immediate Early Gene Express and Replication in Vitro," Molecular Medicine Reports, 2014, vol. 9, pp. 744-748.

*Primary Examiner* — Susan Hoffman
(74) *Attorney, Agent, or Firm* — Fish & Richardson P.C.

(57) ABSTRACT

The present invention relates to a pharmaceutical composition for preventing or treating alpha-herpesvirus infection comprising an *Elaeocarpus sylvestris* extract or a fraction thereof as an active ingredient, and can effectively prevent, treat or alleviate an alpha-herpesvirus and diseases caused thereby, such as herpes, encephalitis, genital herpes, chicken pox, or herpes zoster.

6 Claims, 16 Drawing Sheets

PHARMACEUTICAL COMPOSITION FOR PREVENTING AND TREATING ALPHA HERPES VIRUS INFECTION, CONTAINING, AS ACTIVE INGREDIENT, *ELAEOCARPUS SYLVESTRIS* EXTRACT OR FRACTION THEREOF

CROSS-REFERENCE TO RELATED APPLICATIONS

This application is a continuation and claims priority to U.S. patent application Ser. No. 16/331,876 filed Mar. 8, 2019, now abandoned, which is a U.S. National Stage application and claims priority of International Application No. PCT/KR2017/004614. filed Apr. 28, 2017, which claims priority to South Korean Application No. 10-2016-0116611, filed Sep. 9, 2016. The contents of all of the prior applications are incorporated herein by reference in their entirety.

TECHNICAL FIELD

The present invention relates to a pharmaceutical composition for preventing or treating alpha-herpesvirus infection which comprises an *Elaeocarpus sylvestris* extract or a fraction thereof as an active ingredient.

BACKGROUND ART

With increasing stress due to modernization, the incidence of intractable diseases caused by chronic infectious virus is increasing. In particular, the occurrence of varicella and herpes zoster patients due to herpes virus has recently increased rapidly, and infectious diseases caused by such herpes viruses are more common than infection diseases caused by other chronic infectious viruses.

There are eight types of human herpes viruses, which typically include herpes simplex virus (HSV), which causes various herpes, varicella-zoster virus (VZV), human cytomegalovirus (HCMV), which causes giant cell tumors, Epstein-Barr virus (EBV), which causes various tumors, and the like.

Herpes viruses are highly infectious compared to other chronic infectious viruses and have a high infection rate of 70 to 90% or more worldwide. These herpes viruses are typical chronic skin disease viruses that cause various diseases, such as chicken pox, herpes zoster, herpes simplex, genital herpes, conjunctivitis and giant cell tumors by repeating latent infection and reactivation in the host after infecting the host, and maintain infectivity during their lifetime.

Acyclovir is the only antiviral drug for treating such herpes viruses, and accounts for about 74% of the antiviral agent market. Currently commercially available antiviral agents against herpes viruses mostly act on a limited number of virus groups, and problems such as increased tolerance due to the appearance of mutations against these antiviral agents, resulting in low efficiency and various side effects.

However, other agents have not yet been developed, and there are no preventive vaccines or therapeutic vaccines against the seven human herpes viruses other than a live vaccine for prevention of varicella zoster virus (VZV).

Therefore, for chronic infectious viral diseases, continuous administration of antiviral agents is required in many cases, but causes serious side effects. Thus, it is required to develop a therapeutic agent against chronic infectious viral diseases, which has relatively less side effects and is based on a natural substance.

DISCLOSURE

Technical Problem

The present invention provides a pharmaceutical composition for preventing and treating alpha-herpesvirus infection, which comprises an *Elaeocarpus sylvestris* extract or a fraction thereof as an active ingredient.

The present invention also provides a formulation for preventing and treating alpha-herpesvirus infection, which comprises the pharmaceutical composition.

The present invention also provides a health food for preventing and alleviating alpha-herpesvirus infection, which comprises an *Elaeocarpus sylvestris* extract or a fraction thereof as an active ingredient.

The present invention also provides a method for preventing and treating alpha-herpesvirus infection, which comprises a step of administering to a subject a pharmaceutical composition comprising an *Elaeocarpus sylvestris* extract or a fraction thereof.

The present invention also provides the use of an *Elaeocarpus sylvestris* extract or a fraction thereof for preventing or treating alpha-herpesvirus infection.

The present invention also provides the use of a pharmaceutical composition comprising an *Elaeocarpus sylvestris* extract or a fraction thereof in manufacture of a medicament for prevention or treatment of alpha-herpesvirus infection.

Technical Solution

The present inventors have conducted extensive studies to find a natural substance having little or no side effects while having antiviral efficacy, and as a result, have found that an *Elaeocarpus sylvestris* extract or a fraction thereof exhibits an excellent effect on the inhibition of replication of alpha-herpesvirus and also exhibits excellent viral replication inhibitory activity in alpha-herpesvirus infection animal models, thereby completing the present invention.

Advantageous Effects

A pharmaceutical composition comprising an *Elaeocarpus sylvestris* extract or a fraction thereof as an active ingredient according to the present invention effectively inhibits alpha-herpesvirus, and thus can prevent, treat or alleviate alpha-herpesvirus and diseases caused thereby, such as herpes, encephalitis, genital herpes, chickenpox, herpes zoster, and the like, and also has an inhibitory effect against peripheral and central inflammatory pain that can be caused by herpes or the like.

BEST MODE

Figure 1:
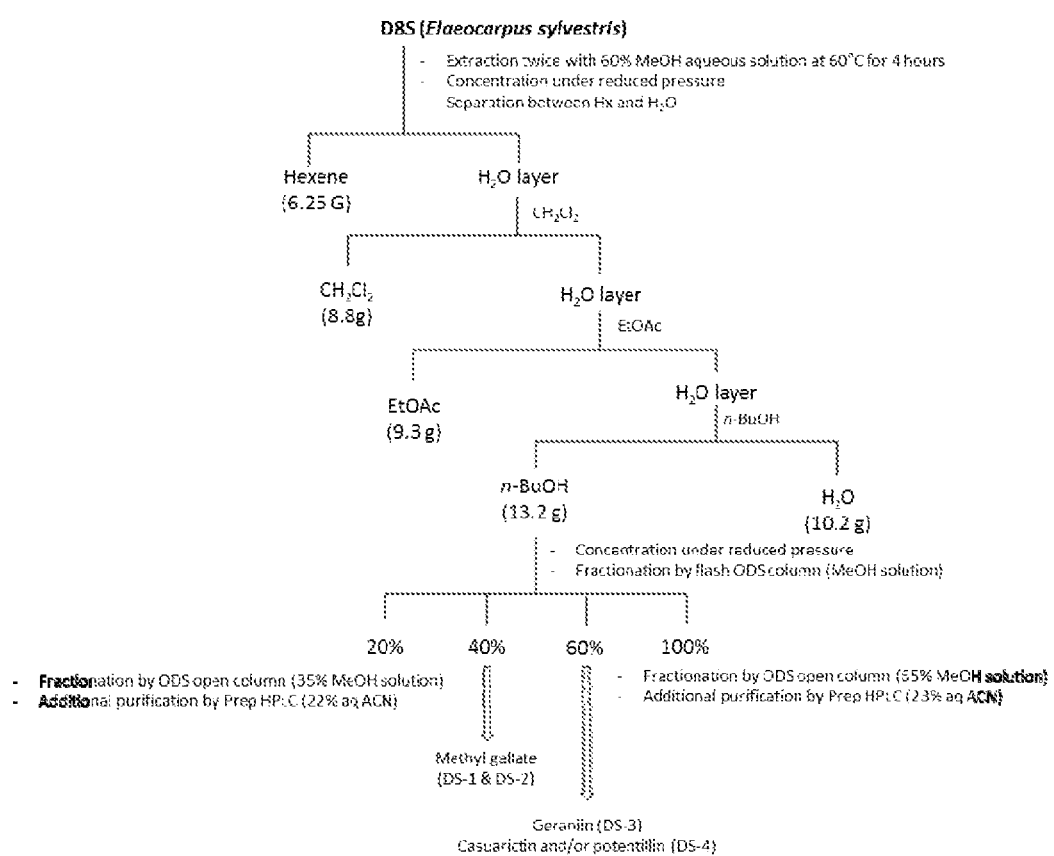
FIG. 1 shows a process of obtaining a dichloromethane fraction from an *Elaeocarpus sylvestris* extract of the present invention and a process of separating methyl gallate (DS-1 and DS-2), geraniin (DS-3) and casuarictin (DS-4) therefrom.
Figure 2:
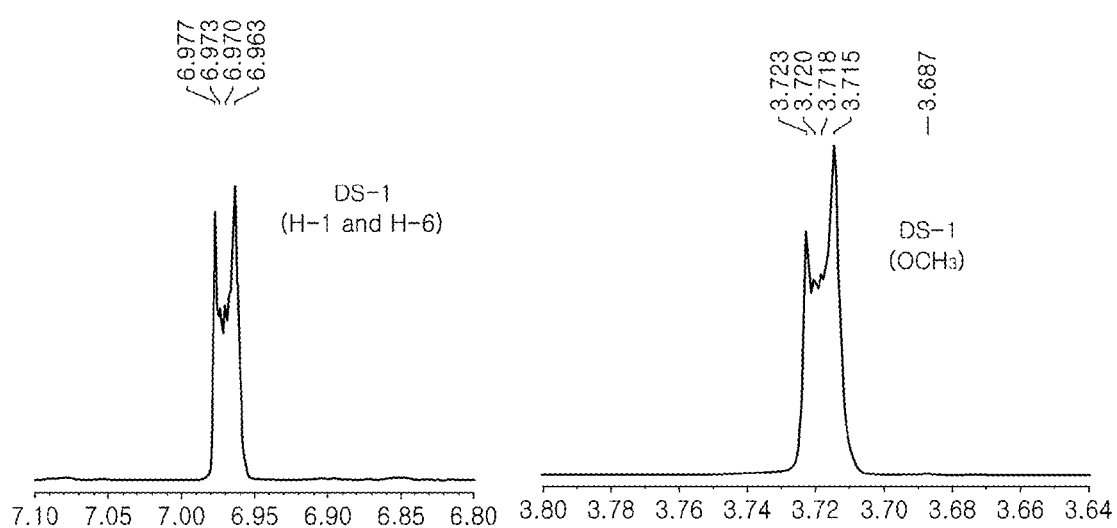
FIG. 2 shows the NMR spectrum of methyl gallate (DS-1) separated from an *Elaeocarpus sylvestris* extract according to an example of the present invention.
Figure 3:
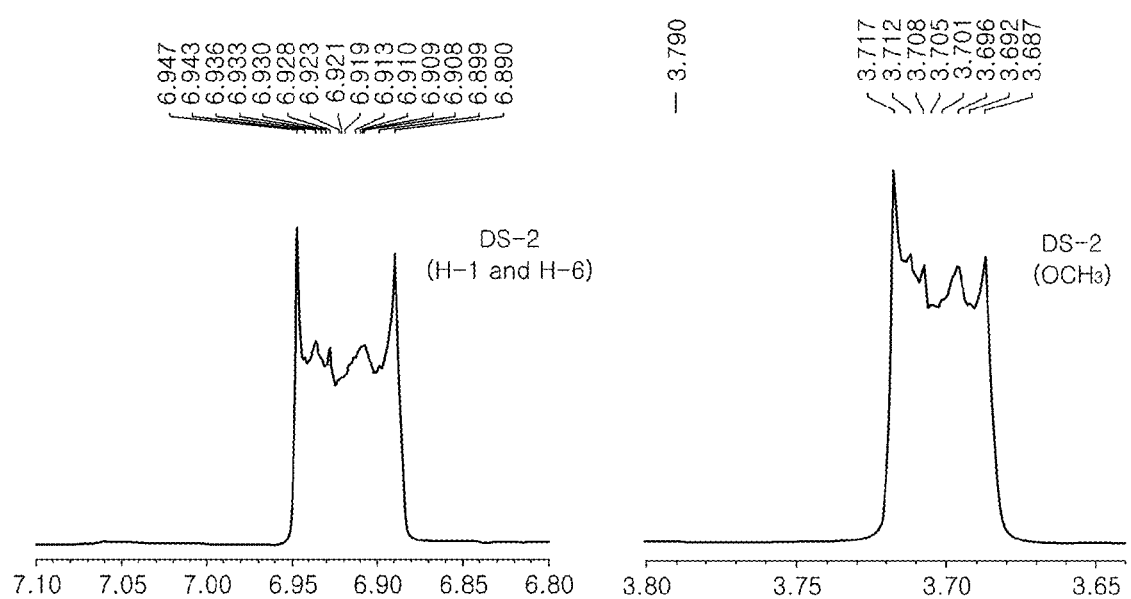
FIG. 3 shows the NMR spectrum of methyl gallate (DS-2) separated from an *Elaeocarpus sylvestris* extract according to an example of the present invention.
Figure 4:
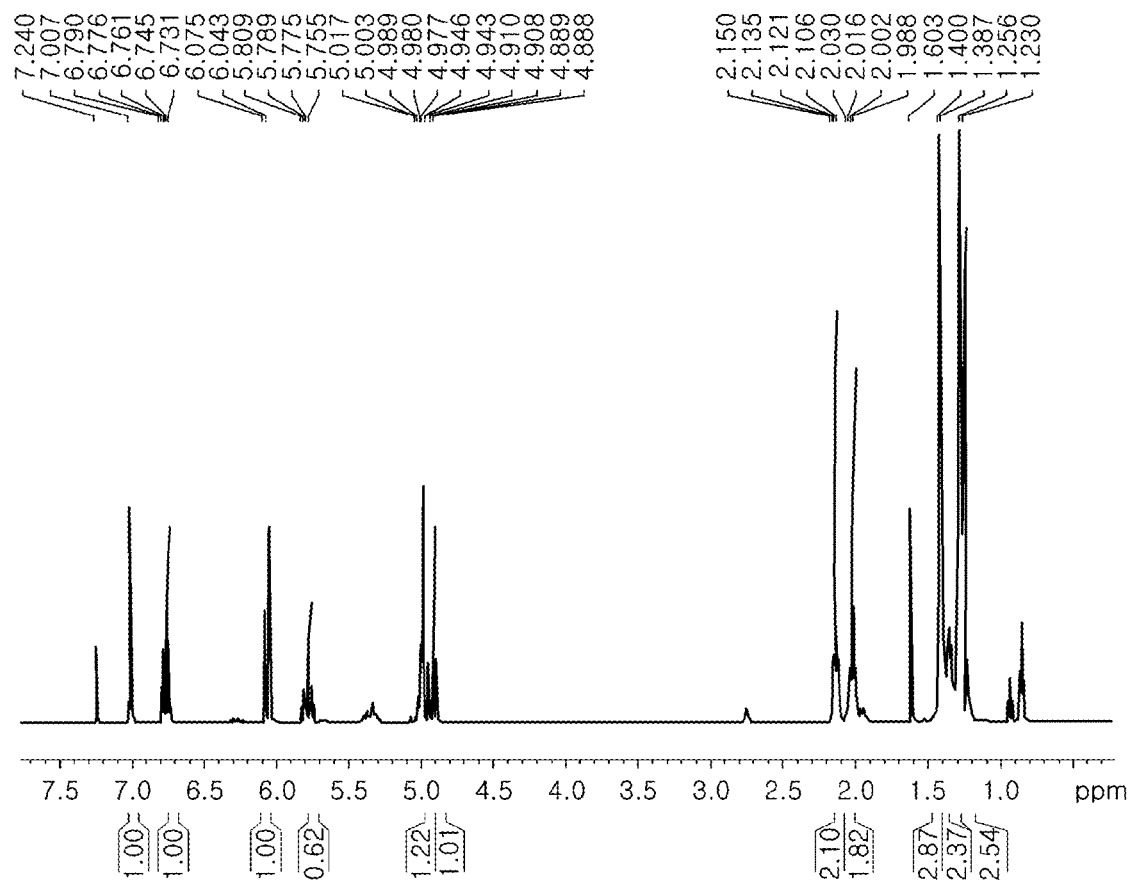
FIG. 4 shows the NMR spectrum of geraniin (DS-3) separated from an *Elaeocarpus sylvestris* extract according to an example of the present invention.
Figure 5:
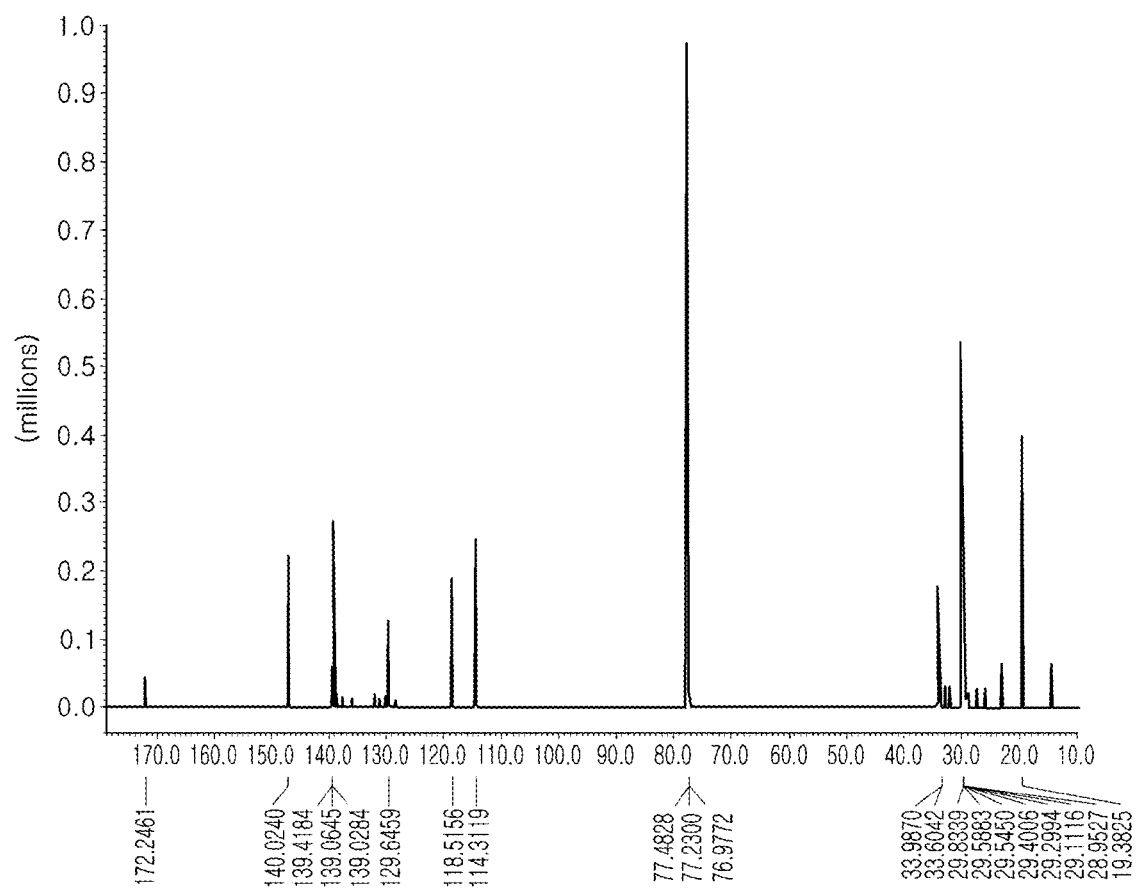
FIG. 5 shows the NMR spectrum of casuarictin (DS-4) separated from an *Elaeocarpus sylvestris* extract according to an example of the present invention.

Hereinafter, the present invention will be described in detail.

In a first aspect of the present invention, the present invention provides a pharmaceutical composition for preventing and treating alpha-herpesvirus infection, which comprises an *Elaeocarpus sylvestris* extract or a fraction thereof as an active ingredient.

The alpha-herpesvirus may be one or more viruses selected from among varicella-zoster virus (VZV), herpes simplex virus-1 (HSV-1) and herpes simplex virus-2 (HSV-2).

The alpha-herpesvirus infection refers to infection with herpes viruses, which manifest latent and infectious symptoms in the nervous system, such as varicella-zoster virus (VZV), herpes simplex virus-1 (HSV-1) and herpes simplex virus-2 (HSV-2). The disease caused by this infection may be any one or more selected from among herpes, genital herpes, chickenpox, and herpes zoster. In addition, if herpes such as herpes zoster is caused by the alpha-herpesvirus infection, peripheral and central inflammatory pain or the like may occur.

The *Elaeocarpus sylvestris* extract of the present invention may be an extract obtained from a leaf, fruit or stem part which is the aerial part of a cultivated or commercially available plant, but is not limited thereto. Preferably, the *Elaeocarpus sylvestris* extract of the present invention may be an extract obtained from the fruit of *Elaeocarpus sylvestris*.

The *Elaeocarpus sylvestris* extract of the present invention may include a water or organic solvent extract. Preferably, it may be an organic solvent extract, a crude extract, or a concentrate thereof.

The organic solvent is preferably one or more selected from the group consisting of a lower alcohol having 1 to 4 carbon atoms, hexane, ethyl acetate, dichloromethane, ether, chloroform, and acetone. The lower alcohol having 1 to 4 carbon atoms is preferably one or more selected from the group consisting of methanol, ethanol, propanol, isopropanol, butanol and n-butanol, and the lower alcohol having 1 to 4 carbon atoms may include an anhydrous or hydrated alcohol having 1 to 4 carbon atoms. The alcohol, for example, preferably ethanol or isopropanol, may be 1 to 100% (v/v), preferably 30 to 100%, more preferably 30 to 80%, even more preferably 30%, 35%, 40%, 45%, 50%, 55%, 60%, 65%, or 70% alcohol.

According to one embodiment of the present invention, the *Elaeocarpus sylvestris* extract is preferably a heated extract obtained by heating and extraction with 50% ethanol.

In addition, a fraction of the *Elaeocarpus sylvestris* extract of the present invention may be a fraction (secondary extract) obtained by concentrating a crude extract of *Elaeocarpus sylvestris* (primary extract) and fractionating the concentrate by adding lower alcohols having 1 to 4 carbon atoms, aqueous solutions thereof or non-polar solvents individually (or in combination).

According to one embodiment of the present invention, the fraction of *Elaeocarpus sylvestris* may be prepared by extracting the fruits of *Elaeocarpus sylvestris* with methanol to obtain a methanol extract (primary extract), suspending the methanol extract in water, and fractionating the suspension sequentially with n-hexane, dichloromethane, ethyl acetate and n-butanol, followed by vacuum concentration.

In order to prepare an active fraction having higher physiological activity from the above-described fraction, the butanol fraction from the water fraction may be subjected to silica gel column chromatography, thereby preparing an active fraction. At this time, the active fraction may be prepared by performing silica gel column chromatography using a solvent mixture of ethyl acetate and methanol (80:20→0:100), drying the fraction under vacuum, and purifying the dried fraction by preparative HPLC.

According to one embodiment of the present invention, the following compounds may be separated from the *Elaeocarpus sylvestris* extract of the present invention:

Methyl gallate represented by the following formula 1a:

[Formula 1a]

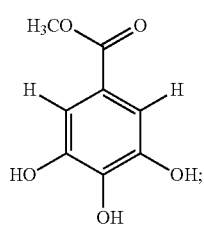

Geraniin represented by the following formula 1b:

[Formula 1b]

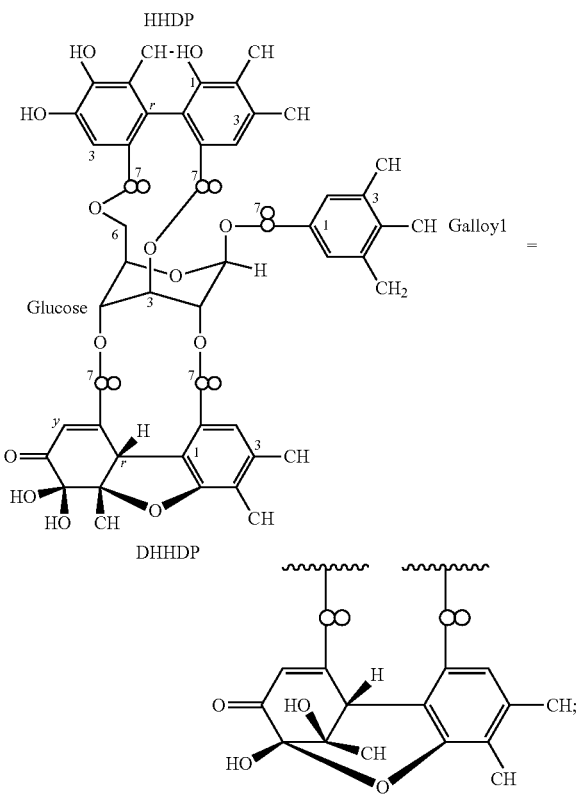

and
Casuarictin represented by the following formula 1c:

[Formula 1c]

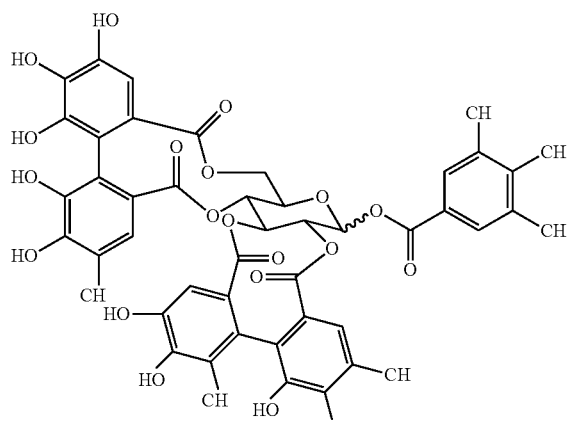

Casunrictin: β-galloyl
Potentillin: α-galloyl

These compounds may be obtained by organic synthesis or may be natural substances obtained from plants.

The *Elaeocarpus sylvestris* extract of the present invention may include not only an extract obtained using the above-described extraction solvent, but also an extract subjected to a conventional purification process. For example, fractions obtained through various additional purification methods, such as separation with an ultrafiltration membrane having a given molecular weight cut-off, separation by various chromatography systems (manufactured for separation according to size, charge, hydrophobicity or affinity), or the like, are also included in the scope of the fraction of the present invention.

The *Elaeocarpus sylvestris* extract or fraction thereof according to the present invention may be prepared into powder by a conventional drying process, such as vacuum drying, spray-drying or freeze-drying, in order to remove the remaining lower alcohol and organic solvent so as to be suitable for use as a pharmaceutical raw material.

It was confirmed that a pharmaceutical composition containing any one or more selected from the group consisting of the *Elaeocarpus sylvestris* extract of the present invention, a fraction thereof, and methyl gallate, geraniin and casuarictin, which are components separated therefrom, has the effect of efficiently inhibiting the replication of herpes virus by inhibiting the expression of replication-related genes in alpha-herpesvirus infection animal models.

The *Elaeocarpus sylvestris* extract of the present invention comprises any one or more selected from the group consisting of methyl gallate, geraniin and casuarictin.

The present invention provides a pharmaceutical composition for preventing and treating alpha-herpesvirus infection, which comprises, as an active ingredient, any one selected from the group consisting of methyl gallate, geraniin and casuarictin.

In a second aspect of the present invention, the present invention provides a formulation for preventing and treating alpha-herpesvirus infection, which comprises the pharmaceutical composition.

Accordingly, the pharmaceutical composition of the present invention may be formulated as oral dosage forms, for example, tablets, troches, lozenges, aqueous or oily suspensions, crude powders or granules, emulsions, hard or soft capsules, syrups or elixirs, according to conventional methods for preventing and treating alpha-herpesvirus infection.

Formulations, such as tablets and capsules, may contain a binder, such as lactose, saccharose, sorbitol, mannitol, starch, amylopectin, cellulose or gelatin; an excipient such as dicalcium phosphate; a disintegrant, such as corn starch or sweet potato starch; and a lubricant, such as magnesium stearate, calcium stearate, sodium stearyl fumarate or polyethylene glycol wax. Capsule formulations may contain, in addition to the above-mentioned materials, a liquid carrier such as fatty oil.

In addition, the pharmaceutical composition of the present invention may be administered parenterally, and the parenteral administration may be done by subcutaneous injection, intravenous injection, intramuscular injection or intra-thoracic injection. To prepare a formulation for parenteral administration, the composition may be mixed with a stabilizer or a buffer in water to obtain a solution which may then be formulated as a unit dosage form such as an ampoule or a vial.

The pharmaceutical composition of the present invention may be administered in a pharmaceutically effective amount. As used herein, the term "pharmaceutically effective amount" refers to an amount sufficient to treat diseases, at a reasonable benefit/risk ratio applicable to any medical treatment. The effective dosage level may be determined depending on various factors, including a formulation method, the patient's condition and weight, the patient's sex and age, the disease severity, the form of drug, the route and duration of administration, excretion rate, responsiveness, and the like. The effective amount may vary depending on the route of treatment, the use of excipients, and the likelihood of use with other agents, as appreciated by those skilled in the art.

Although the dosage or dose of the pharmaceutical composition comprising the *Elaeocarpus sylvestris* extract or a fraction thereof as an active ingredient according to the present invention may vary depending on the patient's age, physical condition, weight, and the like, it is preferably administered at a dose of 10 to 100 mg/kg (weight)/day. In addition, it may be administered once or several times a day within the daily dose range.

In a third aspect of the present invention, the present invention provides a health food for preventing and alleviating alpha-herpesvirus infection, which comprises an *Elaeocarpus sylvestris* extract or a fraction thereof as an active ingredient.

The *Elaeocarpus sylvestris* extract or fraction thereof according to the present invention, when contained in a food and taken, exhibits the effect of inhibiting alpha-herpesvirus infection, and thus can effectively prevent, treat or alleviate alpha-herpesvirus infection and diseases caused thereby.

The *Elaeocarpus sylvestris* extract or fraction thereof of the present invention may be added to or used together with other foods or food components, and may be suitably used according to conventional methods.

There is no particular limit to the kind of the above-described food. Examples of foods to which the *Elaeocarpus sylvestris* extract or a fraction thereof may be added include meats, sausages, bread, chocolate, candies, snack, confectionery, pizza, noodles, gum, dairy products including ice cream, various soups, beverages, teas, drinks, alcoholic beverages and multi-vitamin preparations. The foods include all health foods in a conventional sense. In addition, the food composition containing the *Elaeocarpus sylvestris* extract or fraction thereof of the present invention may contain various nutritional supplements, vitamins, electrolytes, flavoring agents, coloring agents, pectic acid and its salt, alginic acid and its salt, organic acids, protective colloids, thickeners, pH adjusters, stabilizers, preservatives, glycerin, alcohols, carbonizing agents that are used in carbonated beverages, etc. In addition, the food composition containing the *Elaeocarpus sylvestris* extract or fraction thereof of the present invention may contain fruit fresh for preparation of natural fruit juice beverages, fruit juice beverages and vegetable juices. These components may be used individually or as a mixture.

The present invention also provides a method for preventing and treating alpha-herpesvirus infection, comprising a step of administering to a subject a pharmaceutical composition comprising an *Elaeocarpus sylvestris* extract or a fraction thereof.

As used herein, the terms "*Elaeocarpus sylvestris* extract", "fraction of *Elaeocarpus sylvestris* extract", and "alpha-herpesvirus infection" are as described above.

As used herein, the term "subject" may mean all animals, including humans who have, or are at risk of, developing alpha-herpesvirus infection.

Specifically, the preventing or treating method of the present invention may comprise a step of administering a pharmaceutically effective amount of the composition to a subject having or being at risk of developing alpha-herpesvirus infection.

As used herein, the term "effective amount" is as defined above.

The present invention also provides the use of an *Elaeocarpus sylvestris* extract or a fraction thereof for preventing or treating alpha-herpesvirus infection.

The present invention also provides the use of a pharmaceutical composition comprising an *Elaeocarpus sylvestris* extract or a fraction thereof in manufacture of a medicament for prevention or treatment of alpha-herpesvirus infection.

The *Elaeocarpus sylvestris* extract or fraction thereof for manufacture of the medicament may be mixed with a pharmaceutically acceptable carrier, excipient or diluent. In addition, it may be combined with other active agents to provide a combination formulation having a synergistic effect.

MODE FOR INVENTION

The numerical values described in the specification should be construed as including equivalent ranges unless otherwise indicated.

Hereinafter, preferred preparation examples, examples and formulation examples will be presented to facilitate understanding of the present invention. However, these preparation examples, examples and formulation examples are merely provided to facilitate the understanding of the present invention, and the scope of the present invention is not limited by these preparation examples, examples and formulation examples.

EXAMPLES

Preparation Example 1: Preparation of *Elaeocarpus sylvestris* Extract and Fraction 1-1. Preparation of Ethanol Extract

*Elaeocarpus sylvestris* produced in Jeju Island, Korea, was purchased and dried, and then 250 g of the *Elaeocarpus sylvestris* fruits were extracted with various concentrations of ethanol (aqueous ethanol solution or 0%, 30%, 50%, 70% and 100% ethanol) at room temperature for 24 hours. As a result, *Elaeocarpus sylvestris* extracts were obtained in amounts of 31.35 g (12.54% yield), 61.67 g (24.67% yield), 76.17 g (30.47% yield), 79.6 g (31.84% yield) and 37.22 g (14.89% yield) for the various concentrations of ethanol, respectively.

1-2: Preparation of Ethanol Heated Extracts 250 g of dried *Elaeocarpus sylvestris* fruits were extracted with various concentrations (%) of ethanol in a heating extractor at 70 to 80° C. for 3 hours. As a result, heated *Elaeocarpus sylvestris* extracts were obtained in amounts of 38.42 g (15.37% yield), 71.9 g (28.77% yield), 80.85 g (32.34% yield), 83.45 g (33.38% yield), and 45.67 g (18.27% yield) for various ethanol concentrations (0, 30, 50, 70 and 100% ethanol), respectively.

1-3: Preparation and Analysis of Fraction of 50% Ethanol Extract 50 g of the *Elaeocarpus sylvestris* extract obtained in Preparation Example 1-1 was suspended in 2 L of distilled water, and then fractionated sequentially with the same amounts of n-hexane (Hx), dichloromethane (MC), ethyl acetate (EA) and n-butanol (BuOH), followed by vacuum concentration, thereby obtaining a butanol extract.

The obtained butanol fraction was subjected to silica gel column chromatography (20 to 100% MeOH) packed with silica beads), thereby obtaining four sub-fractions. Among the obtained sub-fractions, the second sub-fraction (40% MeOH) and the third sub-fraction (60% MeOH) were fractionated again with 35% MeOH and 65% MeOH, respectively, by a TLC plate. From the second sub-fraction, fraction 1 (DS-1) and fraction 2 (DS-2) were collected, and from the third sub-fraction, fraction 3 (DS-3) and fraction 4 (DS-4) were collected. These fractions were structurally identified by NMR. The results of structural identification of DS-1, DS-2, DS-3 and DS-4 are shown in Tables 1 to 4 below and FIGS. 2 to 5.

TABLE 1

Results of NMR structural identification of DS-1
NMR data of sample DS-1

| | C | H |
|---|---|---|
| C=O | 169.17 | |
| 3,5 | 144.71 × 2 | |
| 4 | 138.25 | |
| 1 | 120.89 | |
| 2,6 | 110.01 × 2 | 6.97 (2H, s) |
| OCH$_3$ | 52.66 | 3.72 (3H, s) |
| CD$_3$$\underline{C}$O$_2$D | 177.02 | Additive (acetic acid) |
| $\underline{C}$D$_3$CO$_2$D | 20.00 | |

TABLE 2

Results of NMR structural identification of DS-2
NMR data of sample DS-2

| | C | H |
|---|---|---|
| C=O | 169.11 | |
| 3,5 | 144.64 × 2 | |
| 4 | 138.19 | |
| 1 | 120.81 | |
| 2,6 | 109.95 × 2 | 6.91 (2H, s) |
| OCH$_3$ | 52.63 | 3.69 (3H, s) |
| CD$_3$$\underline{C}$O$_2$D | 177.04 | Additive (acetic acid) |
| $\underline{C}$D$_3$CO$_2$D | 19.99 | |

TABLE 3

Results of NMR structural identification of DS-3
$^1$H & $^{13}$C-NMR data (CD$_3$OD-d$_4$) of sample DS-3

| | C | H | |
|---|---|---|---|
| 1 | 195.31 | | 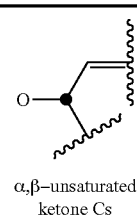 |
| 2 | 192.35 | | |
| | | | α,β–unsaturated ketone Cs |
| 1 | 170.10 | | 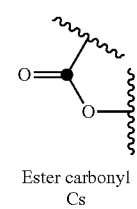 [SMILES: *OC(*)=O] |
| 2 | 167.58 | | |
| 3 | 166.47 | | |
| 4 | 166.36 | | |
| 5 | 166.19 | | |
| 6 | 166.12 | | |
| 7 | 166.08 | | |
| 8 | 165.67 | | |
| | | | Ester carbonyl Cs |

TABLE 3-continued

Results of NMR structural identification of DS-3
$^1$H & $^{13}$C-NMR data (CD$_3$OD-d$_4$) of sample DS-3

| | C | H | |
|---|---|---|---|
| 1 | 148.31 | | |
| 2 | 147.17 | | |
| 3, 4 | 146.47 × 2 | | |
| 5, 6 | 146.44 × 2 | | |
| 7 | 146.39 | | |
| 8 | 146.15 | | |
| 9 | 146.09 | | |
| 10 | 145.62 | | Oxidized sp2-tert Cs |
| 11 | 145.55 | | |
| 12 | 145.53 | | |
| 13 | 145.52 | | |
| 14 | 145.28 | | |
| 15 | 145.26 | | |
| 16 | 143.32 | | |
| 17 | 140.93 | | |
| 18 | 140.88 | | |
| 19 | 139.83 | | |
| 20 | 138.86 | | |
| 21 | 138.77 | | |
| 22 | 138.16 | | |
| 23 | 137.54 | | |
| 24 | 137.53 | | |
| 1 | 125.67 | | |
| 2 | 125.48 | | |
| 3 | 124.24 | | |
| 4 | 124.19 | | |
| 5 | 120.16 | | |
| 6 | 120.06 | | |
| 7 | 120.04 | | |
| 8 | 119.20 | | |
| | | | sp2-tert Cs (C$_{sp2}$-carbonyl) |
| 1 | 130.21 | 6.58 (1H, s) | |
| 2 | 125.07 | 6.24 (1H, s) | α,β–unsaturated ketone α-Cs |
| 1 | 117.69 | | |
| 2 | 117.57 | | |
| 3 | 117.13 | | |
| 4, 5 | 116.12 × 2 | | |
| 6 | 115.44 | | sp2-tert Cs (C-C) |
| 1 | 114.46 | 7.25 (1H, s) | |
| 2 | 114.14 | 7.23 (1H, s) | |
| 3, 4 | 111.21 × 2 | 7.12 (2H, s) | |
| 5, 6 | 111.02 × 2 | 7.10 (2H, s) | |
| 7 | 110.89 | 6.93 (1H, s) | |
| 8 | 110.66 | 6.89 (1H, s) | sp2-methine Cs |

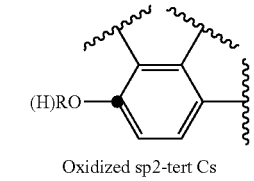
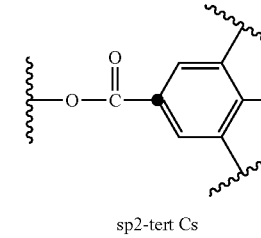
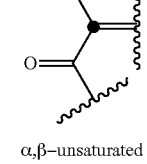
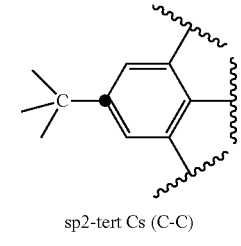 [SMILES: *c1cc(C(C)(C)C)cc(*)c1*]

TABLE 3-continued

Results of NMR structural identification of DS-3
$^1$H & $^{13}$C-NMR data (CD$_3$OD-d$_4$) of sample DS-3

| | C | H | |
|---|---|---|---|
| 1 | 108.70 | | |
| 2 | 96.45 | | |
| 3 | 96.37 | | |
| 4 | 95.85 | | 2-oxidized sp3-tert Cs |
| 1 | 52.61 | 4.95 (1H, s) | |
| 2 | 42.05 | 5.45 (1H, s) | sp3-methine Cs |
| 1 | 92.67 | 6.63 (1H, s) | Sugar |
| 1' | 91.67 | 6.57 (1H, s) | |
| 2 | 67.21 | 5.40 (1H, br s) | |
| 2' | 66.44 | 5.56 (1H, br s) | |
| 3 | 70.63 | 5.47 (1H, br s) | |
| 3' | 70.16 | 5.50 (1H, br s) | |
| 4 | 63.90 | 5.48 (1H, br s) | |
| 4' | 62.92 | 5.39 (1H, br s) | |
| 5 | 73.52 | 4.81 (1H, br s) | |
| 5' | 73.31 | 4.83 (1H, br s) | |
| 6 | 64.58 | 4.39 (1H), 4.92 (1H) | |
| 6' | 64.37 | 4.30 (1H), 5.54 (1H) | |

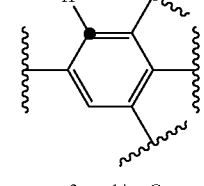
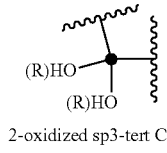

TABLE 4

Results of NMR structural identification of DS-3
$^1$H & $^{13}$C-NMR data (CD$_3$OD-d$_4$) of sample DS-3

| | C | H | |
|---|---|---|---|
| 1 | 170.92 | | |
| 2 | 170.17 | | |
| 3 | 167.62 | | |
| 4 | 166.51 | | |
| 5 | 166.39 | | Ester carbonyl Cs |
| 1 | 147.37 | | |
| 2-4 | 146.56 × 3 | | |
| 5, 6 | 146.50 × 2 | | |
| 7 | 146.18 | | |
| 8 | 145.92 | | |
| 9 | 145.65 | | |
| 10 | 145.60 | | |
| 11 | 145.36 | | Oxidized sp2-tert Cs |
| 12 | 141.40 | | |
| 13 | 140.95 | | |
| 14 | 138.75 | | |
| 15 | 137.58 | | |

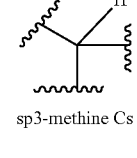
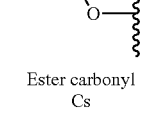
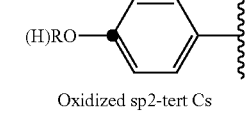

TABLE 4-continued

Results of NMR structural identification of DS-3
$^1$H & $^{13}$C-NMR data (CD$_3$OD-d$_4$) of sample DS-3

| | C | H | |
|---|---|---|---|
| 1 | 125.37 | | |
| 2 | 124.54 | | |
| 3 | 120.11 | | |
| 4 | 117.74 | | |
| 5 | 117.64 | | | sp2-tert Cs
(C$_{sp2}$-carbonyl)

| 1 | 116.24 |
| 2 | 116.07 |
| 3 | 110.54 |
| 4 | 110.40 | sp2-tert Cs (C-C)

| 1, 2 | 110.92 × 2 | 7.08 (2H, s) |
| 3 | 110.65 | 7.47 (1H, s) |
| 4 | 108.28 | 7.09 (1H, s) |
| 5 | 105.45 | 6.95 (1H, s) |
| 6 | 103.13 | 6.83 (1H, s) | sp2-methine Cs

| 1 | 92.57 | Overlapped | Sugar |
| 2 | 71.00/66.7 | with H$_2$O | |
| 3 | 66.53 | | |
| 4 | 64.53 | | |
| 5 | 74.22 | | |
| 6 | 62.40 | | |

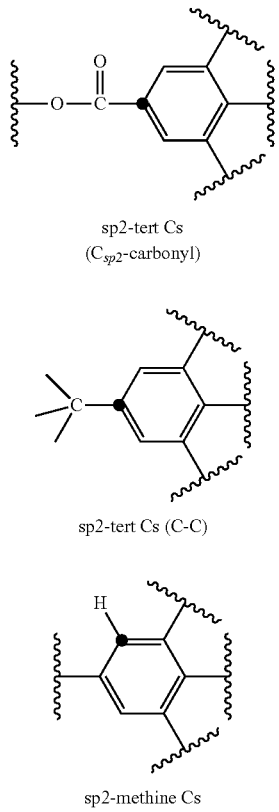

As shown in Tables 1 to 4 above and FIGS. 2 to 5, it was confirmed that DS-1 and DS-2 of the dichloromethane fraction of *Elaeocarpus sylvestris* were methyl gallate (formula 1a), DS-3 was geraniin (formula 1b), and DS-4 was casuarictin (formula 1c).

Preparation Example 2: Mass Production of 50% Ethanol Extract of *Elaeocarpus sylvestris*

In order to prepare an *Elaeocarpus sylvestris* extract containing methyl gallate, geraniin and casuarictin as confirmed in Preparation Example 1-3 above, 100 kg of *Elaeocarpus sylvestris* was added to 1000 L of 50% ethanol and extracted by stirring at 70 to 80° C. for 3 hours, and the extract was cooled to 50° C. or below, and then subjected to first filtration and second filtration. The extract subjected to second filtration was concentrated at 45° C. or below, freeze-dried at −180 to 190° C., and then packaged. The yield of the obtained extract is shown in Table 5 below.

TABLE 5

| Amount produced | Amount packaged | Loss | Extraction yield | Product yield |
|---|---|---|---|---|
| 28.1 kg | 28.0 kg | 0.1 kg | 28.1% | 28.0% |

In addition, to evaluate the prepared 50% ethanol extract of *Elaeocarpus sylvestris*, the following tests were performed.

2-1. Bacterial Reverse Mutation Test for 50% Ethanol Extract of *Elaeocarpus sylvestris*

In order to examine whether the extract induces bacterial mutation, a reverse mutation test was performed using *Salmonella typhimurium* TA98, TA100, TA1535 and TA1537, which are histidine auxotrophic strains, and *Escherichia coli* WP2uvrA which is a tryptophan auxotrophic strain, by a direct method and a metabolic activation method. In the test, a preincubation method was used.

The 50% ethanol extract of *Elaeocarpus sylvestris*, prepared in Preparation Example 2 above, was dispersed in sterile distilled water to prepare the highest concentration of the *Elaeocarpus sylvestris* extract which was then serially diluted. Based on a concentration determination test, the following concentrations were applied in the direct method and the metabolic activation method.

For S9 mix (−): 0, 62, 185, 556, 1667, and 5000 μg/plate;
For S9 mix (+): 0, 62, 185, 556, 1667, and 5000 μg/plate.

The strains were treated with the above-described various concentrations of the 50% ethanol extract of *Elaeocarpus sylvestris*, and as a result, an increase in the number of reverse colonies, which could be considered positive compared to the negative control, was not observed regardless of application of the metabolic activation system. This result suggests that the 50% ethanol extract of *Elaeocarpus sylvestris* did not induce reverse mutation under the above-described test conditions.

2-2. Chromosomal Aberration Assay for 50% Ethanol Extract of *Elaeocarpus sylvestris*

The frequency of aberrant metaphase (gap-) was analyzed, and as a result, the group, continuously treated for 24 hours in the direct method, showed frequencies of 0.5, 0.5, 1.0 and 1.5 at negative control and concentrations of 21, 62 and 185 μg/ml, respectively, and when the frequency of aberrant metaphase was compared with the negative control, a statistically significant increase in the frequency could not be observed at all the concentrations of the 50% ethanol extract of *Elaeocarpus sylvestris*.

The group, treated for 6 hours and recovered for 18 hours in the direct method, showed frequencies of 0.5, 1.5, 1.0 and 2.0 at negative control and concentrations of 21, 62 and 185 μg/ml, respectively, and when the frequency of aberrant metaphase was compared with the negative control, a statistically significant increase in the frequency could not be observed at all the concentrations of the *Elaeocarpus sylvestris* extract.

In addition, the group, treated for 6 hours and recovered for 18 hours in the metabolic activation method, showed frequencies of 1.0, 1.0, 1.5 and 0.0 at negative control and concentrations of 62, 185 and 556 μg/ml, when the frequency of aberrant metaphase was compared with the negative control, a statistically significant increase in the frequency could not be observed at all the concentrations of the *Elaeocarpus sylvestris* extract.

In the direct method and the metabolic activation method, the frequencies of polyploidy (PP) and endoreduplication (ER) also did not show a statistically significant increase compared to the negative control. Therefore, it could be confirmed in the chromosomal aberration assay that the extract was safe.

2-3: Micronucleus Assay for 50% Ethanol Extract of *Elaeocarpus sylvestris*

To obtain baseline data for determining whether the extract induces carcinogenicity, a micronucleus assay among genetic toxicology assays was performed using ICR mouse bone marrow cells. The 50% ethanol extract of *Elaeocarpus sylvestris* of the present invention was administered orally to about 8-week-old male mice at doses of 500 mg/kg, 1000 mg/kg and 2000 mg/kg. At 18 to 24 hours after the administration, bone marrow cells were collected, and the frequency of micronucleus induction and the cytotoxicity were assessed.

For each animal, the number of micronucleated poychromatic erythrocytes (MNPCEs) per about 2,000 polychromatic erythrocytes (PCEs) was counted. All the groups administered with the 50% ethanol extract of *Elaeocarpus sylvestris* of the present invention (500 mg/kg, 1000 mg/kg, and 2000 mg/kg) did not show a statistically significant difference from the solvent control group. Meanwhile, it was observed that the frequency of micronucleus induction in a positive control group significantly increased compared to that in the solvent control group (p<0.01).

From the ratio of PCE/(PCE+NCE) that is the index of cytotoxicity, it could be seen that all the groups administered with the 50% ethanol extract of *Elaeocarpus sylvestris* did not show the distinct inhibition of bone marrow cell proliferation compared to the solvent control group. Therefore, it could be confirmed that the 50% ethanol extract of *Elaeocarpus sylvestris* of the present invention did not induce micronuclei in mouse bone marrow cells.

2-4: Single Oral Dose Toxicity Test of 50% Ethanol Extract of *Elaeocarpus sylvestris* in Rodents To examine toxic symptoms and lethal dose 50 ($LD_{50}$), the *Elaeocarpus sylvestris* extract was administered once orally to male and female Sprague-Dawley (SD) rats. The test was performed on a vehicle control group and a 3,000 mg/kg dose test group. During the test period, the presence or absence of dead animals, general symptoms, weight changes, and autopsy findings of surviving animals at the end of the test were examined.

During the test period, dead animals or unusual general symptoms were not observed, and body weight measurements showed normal body weight gain in all the test animals. In addition, no statistically significant difference in body weight between the test groups was observed. At the end of the test, all surviving animals were biopsied, and as a result, specific visual findings were not observed.

Therefore, under the test conditions, toxic symptoms caused by the 50% ethanol extract of *Elaeocarpus sylvestris* were not observed, and the lethal dose 50 was determined to be 3,000 mg/kg b.w. or more.

2-5: 4-Week Repeated Oral Dose Toxicity Test of 50% Ethanol Extract of *Elaeocarpus sylvestris* in Rodents In order to examine toxic symptoms caused by 28-day repeated oral dose, no observed adverse effect level (NOAEL) and a target organ, male and female Sprague-Dawley (SD) rats were divided into 500 mg/kg, 1000 mg/kg and 2000 mg/kg dose test groups, and comparison with a vehicle control group was performed. During the test period, mortality, general symptoms, weight changes, feed and drinking water intake, eye examination, urinalysis, clinical pathology, organ weight, autopsy findings and histopathological findings were observed.

As a result, during the test period, no dead animal was observed, and sporadic salivation was observed in the *Elaeocarpus sylvestris* extract-administered group immediately administration of the 50% ethanol extract. However, this salivation appeared to be temporal salivation promoted by administration of the 50% ethanol extract of *Elaeocarpus sylvestris* and had no toxicological significance.

In the results of weight change measurement, feed and drinking water intake measurement, eye examination, urinalysis, urine color test, hematological and blood biochemical test, and absolute and relative organ weight measurement, changes associated with the *Elaeocarpus sylvestris* extract were not observed. In addition, in the results of autopsy and histopathological examination, findings and lesions associated with the *Elaeocarpus sylvestris* extract were not observed.

The above-described results suggest that when the 50% ethanol extract of *Elaeocarpus sylvestris* was repeatedly administered orally to the rodent SD rats for 28 days under the test conditions, systemic toxicological changes caused by the *Elaeocarpus sylvestris* were not observed. Thus, the no observed adverse effect level (NOAEL) of the 50% ethanol extract of *Elaeocarpus sylvestris* was determined to be 2,000 mg/kg/day, and no target organ was observed.

2-6: 4-Week Repeated DRF (Dose Range Finding) Oral Dose Toxicity Test of 50% Ethanol Extract of *Elaeocarpus sylvestris* in Non-Rodents In order to examine toxicity appearing when the extract is repeatedly administered orally to non-rodent Beagle dogs and to obtain reference data for use in dose setting for a repeated dose toxicity test to be performed subsequently, an experiment was performed. The dogs were divided into *Elaeocarpus sylvestris* extract groups to be administered with the *Elaeocarpus sylvestris* extract at doses of 250, 500 and 1,000 mg/kg/day and a vehicle control group to be administered with an oral gelatin capsule alone, and the extract was repeatedly administered orally to each group consisting of one male and one female for 4 weeks.

As test and examination items, observation of dead animals and general symptoms, measurement of body weight and feed intake, eye examination, urinalysis, hematological and blood biochemical examination, observation of autopsy findings, organ weight measurement, and observation of histopathological findings were performed.

As a result, no dead animal was observed during the test period, and the results of observation of general symptoms indicated that the remaining feed was observed in the 250, 500 and 1,000 mg/kg/day dose groups, and salivation was observed in the 500 and 1,000 mg/kg/day dose groups, and soft feces and diarrhea were observed in the 1,000 mg/kg/day dose group. The results of observation of weight changes indicated that inhibition of weight gain was observed in the male of the 250 mg/kg/day dose group and in the 500 mg/kg/day dose group, and a decrease in body weight was observed in the female of the 250 mg/kg/day dose group and in the 1,000 mg/kg/day dose group, and a decrease in weight gain was observed in the 250 and 500 mg/kg/day dose groups.

The results of feed intake measurement indicated that a decrease in feed intake was observed in the females of the 250 and 500 mg/kg/day does groups and in the 1,000 mg/kg/day dose group.

The results of eye examination, urinalysis, hematological examination indicated that a toxicologically significant change associated with administration of the *Elaeocarpus sylvestris* extract was not observed.

The results of blood biochemical examination indicated that an increase in ALT (alanine transferase) level was observed in the male of the 500 mg/kg/day dose group and in the 1,000 mg/kg/day dose group and an increase in AST (aspartate aminotransferase) level was observed in the 1,000 mg/kg/day dose group.

The results of organ weight measurement showed that the relative liver weight of the females and males of the groups administered with the *Elaeocarpus sylvestris* extract increased compared to that of the vehicle control group.

Biopsy findings indicated that gray discoloration of the duodenum was observed in the 500 mg/kg/day dose group, and focal white coating of the duodenum was observed in the male of the 1,000 mg/kg/day dose group, and gray and red discoloration of the duodenum was observed in the female of the 1,000 mg/kg/day dose group.

The results of histopathological examination indicated that brown pigment laden macrophages were observed in the duodenal mucosal epitheliums of the males and females of 500 and 1,000 mg/kg dose groups, and focal erosion was observed in the mucosal epithelium of the male of the 1,000 mg/kg dose group, and focal submucosal congestion was observed in the duodenum was observed in the female of the 1,000 mg/kg dose group.

Taken the above results together, it was confirmed that when the 50% ethanol extract of *Elaeocarpus sylvestris* was repeatedly administered orally to the dogs for 4 weeks, observed changes associated with administration of the *Elaeocarpus sylvestris* extract included the remaining feed, salivation, soft feces, diarrhea, weight gain inhibition, weight gain reduction, feed intake reduction, AST and ALT increases, an increase in relative liver weight, duodenal discoloration, brown pigment laden macrophages in duodenal mucosal epitheliums, and the like. In addition, since a decrease in body weight was observed in the female and male of the 1,000 mg/kg dose group during the test period, a high dose group was set to 500 mg/kg/day or less in a repeated dose toxicity test to be subsequently performed using the 50% ethanol extract of *Elaeocarpus sylvestris* of the present invention.

2-7: 13-Week Repeated Oral Dose Toxicity Test of 50% Ethanol Extract of *Elaeocarpus sylvestris* in Rodents In order to examine toxic symptoms caused by 13-week repeated oral dose, no observed adverse effect level (NOAEL) and a target organ, male and female Sprague-Dawley (SD) rats were divided into 500 mg/kg, 1000 mg/kg and 2000 mg/kg dose test groups, and comparison with a vehicle control group was performed. During the test period, mortality, general symptoms, weight changes, feed and drinking water intake, eye examination, urinalysis, clinical pathology, organ weight and visual autopsy findings were examined.

As a result, the no observed adverse effect level (NOAEL) was determined to be 1,000 mg/kg.

2-8: 13-Week Repeated Oral Dose Toxicity Test in Non-Rodents

In order to examine toxicity appearing when the extract is repeatedly administered orally to non-rodent Beagle dogs, the dogs were divided into *Elaeocarpus sylvestris* extract groups to be administered with the *Elaeocarpus sylvestris* extract at doses of 300, 400 and 500 mg/kg/day and a vehicle control group to be administered with an oral gelatin capsule alone, and the extract was repeatedly administered orally to each group consisting of three males and three females for 13 weeks.

As test and examination items, observation of dead animals and general symptoms, measurement of body weight and feed intake, eye examination, urinalysis, hematological and blood biochemical examination, observation of autopsy findings, organ weight measurement, and observation of visual autopsy findings were performed. As a result, the no observed adverse effect level (NOAEL) was determined to be 500 mg/kg.

Example 1: Cell and Virus Culture

Viruses used to measure anti-replication activity were varicella-zoster virus (VZV), herpes simplex virus-1 (HSV-1) and herpes simplex virus-2 (HSV-2), which were obtained from the American Type Culture Collection (ATCC), and MRC-5 and Vero cells were also obtained from the ATCC and cultured. In a 5% $CO_2$ incubator at 37° C., Vero cells were cultured in RPMI1640 medium containing 10% fetal bovine serum and 25 mM HEPES (2-[4-(2-hydroxyethyl) piperazin-1-yl] ethanesulfonic acid), and MRC-5 cells were cultured in MEM medium containing 10% fetal bovine serum and 25 mM HEPES.

Example 2: Test for Evaluation of the Inhibitory Effect of *Elaeocarpus sylvestris* Extract on Expression of HSV Replication-Related Genes HSV is a virus with latent and lytic replication, and comprises a total of three genes: alpha, beta and gamma. The alpha-gene acts as a transcription factor in many cases, the beta-gene is involved in DNA replication, and the gamma-gene acts as a structural gene in most cases. When infected with the virus, a large amount of nonviral mRNA comes out. Based on this fact, monkey kidney epithelial Vero cells which are capable of being infected with HSV-1/2 were infected with HSV-1/2 by culturing them with HSV-1/2-infected cells at a cell-to-cell ratio of 1:8, and an examination was made of what various ethanol extracts of *Elaeocarpus sylvestris* and various heated ethanol extracts of *Elaeocarpus sylvestris* (50 µg/mL) would have effects on the expression level of HSV glycoprotein D (gD) or infected cell protein (ICP0) which has important implications for early protein expression or transcriptional activity and inhibition in viral replication. The results are shown in FIGS. 6 and 7.

Figure 6:
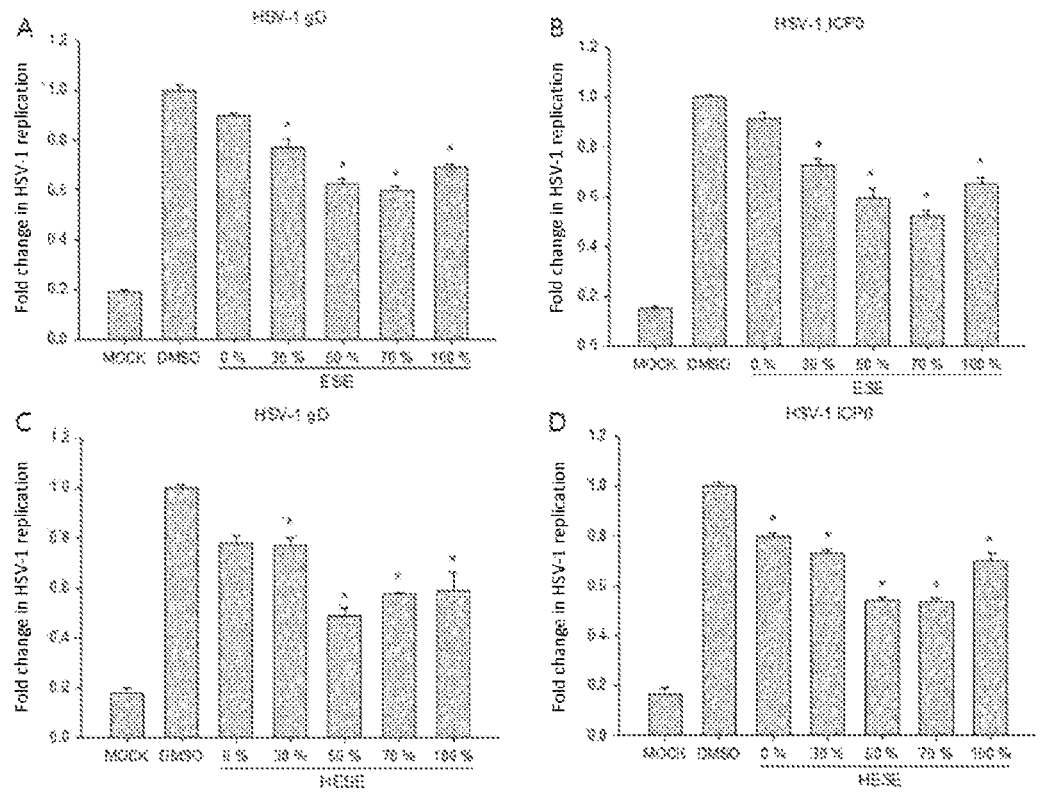
FIG. 6 shows the inhibitory effects of an *Elaeocarpus sylvestris* extract (ESE) and heated *Elaeocarpus sylvestris* extract (HESE) of the present invention on the expression of HSV-1 replication-related genes. Specifically, (A) shows the expression level of HSV-1 gD (glycoprotein D) gene when treated with the *Elaeocarpus sylvestris* extract; (B) shows the expression level of HSV-1 ICP0 (infected cell protein 0) gene when treated with the *Elaeocarpus sylvestris* extract; (C) shows the expression level of HSV-1 gD gene when treated with the heated *Elaeocarpus sylvestris* extract; and (D) shows the expression level of HSV-1 ICP0 gene when treated with the heated *Elaeocarpus sylvestris* extract (* $P<0.05$).
Figure 7:
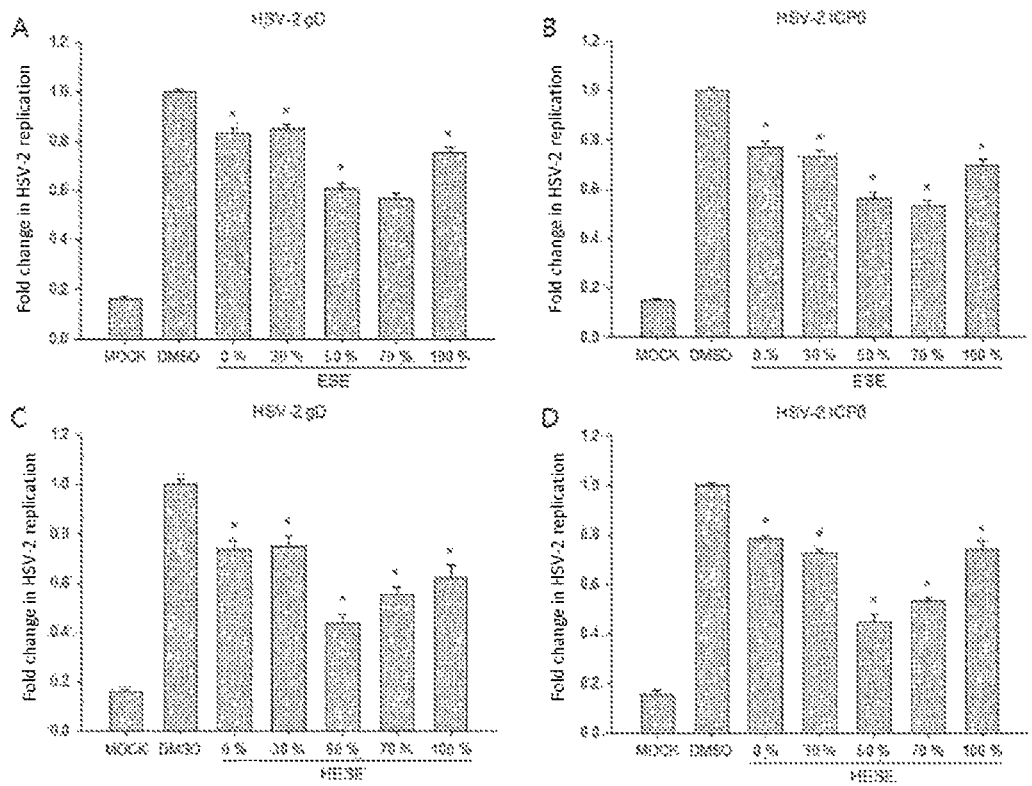
FIG. 7 shows the inhibitory effects of an *Elaeocarpus sylvestris* extract and heated *Elaeocarpus sylvestris* extract of the present invention on the expression of HSV-2 replication-related genes. Specifically, (A) shows the expression level of HSV-2 gD gene when treated with the *Elaeocarpus sylvestris* extract; (B) shows the expression level of HSV-2 ICP0 gene when treated with the *Elaeocarpus sylvestris* extract; (C) shows the expression level of HSV-2 gD gene when treated with the heated *Elaeocarpus sylvestris* extract; and (D) shows the expression level of HSV-2 ICP0 gene when treated with the heated *Elaeocarpus sylvestris* extract (* $P<0.05$).

As shown in FIGS. 6 and 7, among the extracts of *Elaeocarpus sylvestris*, the 70% ethanol extract of *Elaeocarpus sylvestris* showed the best inhibitory effect on the replication of herpes simplex virus-1 (HSV-1) and herpes simplex virus-2 (HSV-2), and among the heated extracts of *Elaeocarpus sylvestris*, the 50% ethanol heated extract showed the best inhibitory effect on viral replication. When the extracts were compared with the heated extracts, the heated extracts showed better inhibitory effects on the replication of HSV-1/2 virus than the extracts obtained at room temperature.

Figure 8:
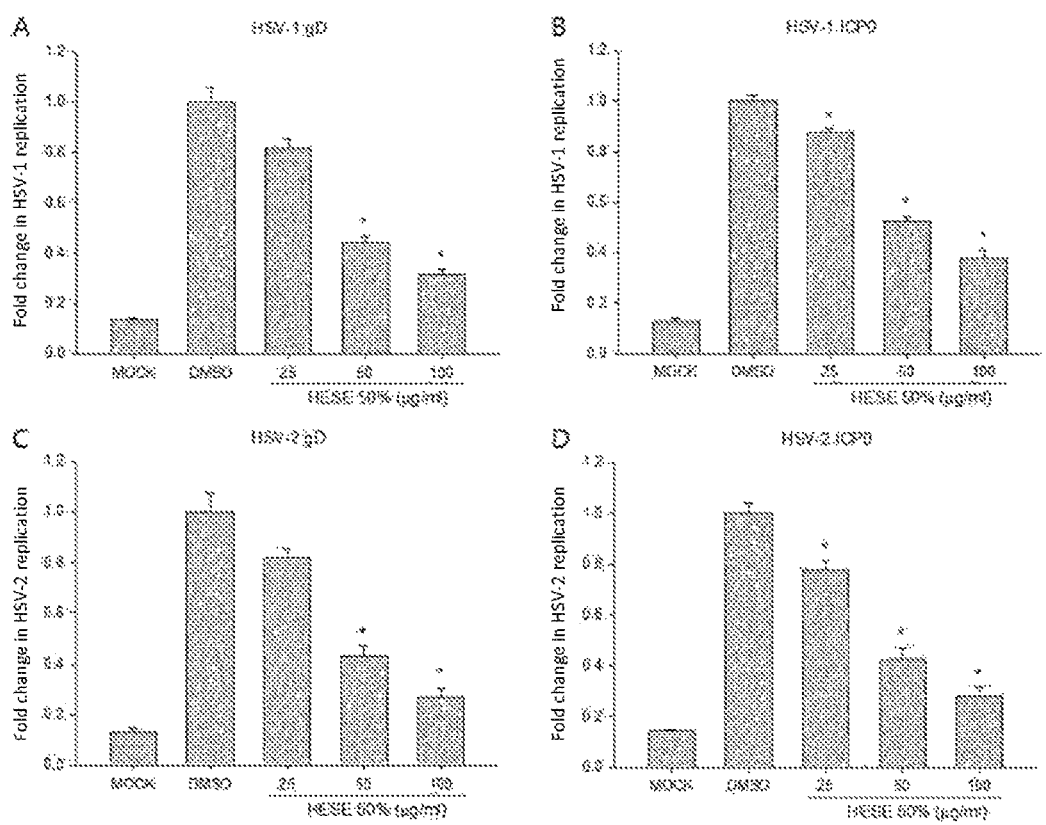
FIG. 8 shows the inhibitory effects of an *Elaeocarpus sylvestris* extract of the present invention on the expression of HSV-1/2 replication-related genes. Specifically, (A) shows the expression level of HSV-1 gD gene when treated with a 50% ethanol heated *Elaeocarpus sylvestris* extract; (B) shows the expression level of HSV-1 ICP0 gene when treated with a 50% ethanol heated *Elaeocarpus sylvestris* extract; (C) shows the expression level of HSV-2 gD gene when treated with a 50% ethanol heated *Elaeocarpus sylvestris* extract; and (D) shows the expression level of HSV-2 ICP0 gene when treated with a 50% ethanol heated *Elaeocarpus sylvestris* extract (* $P<0.05$).
Figure 9:
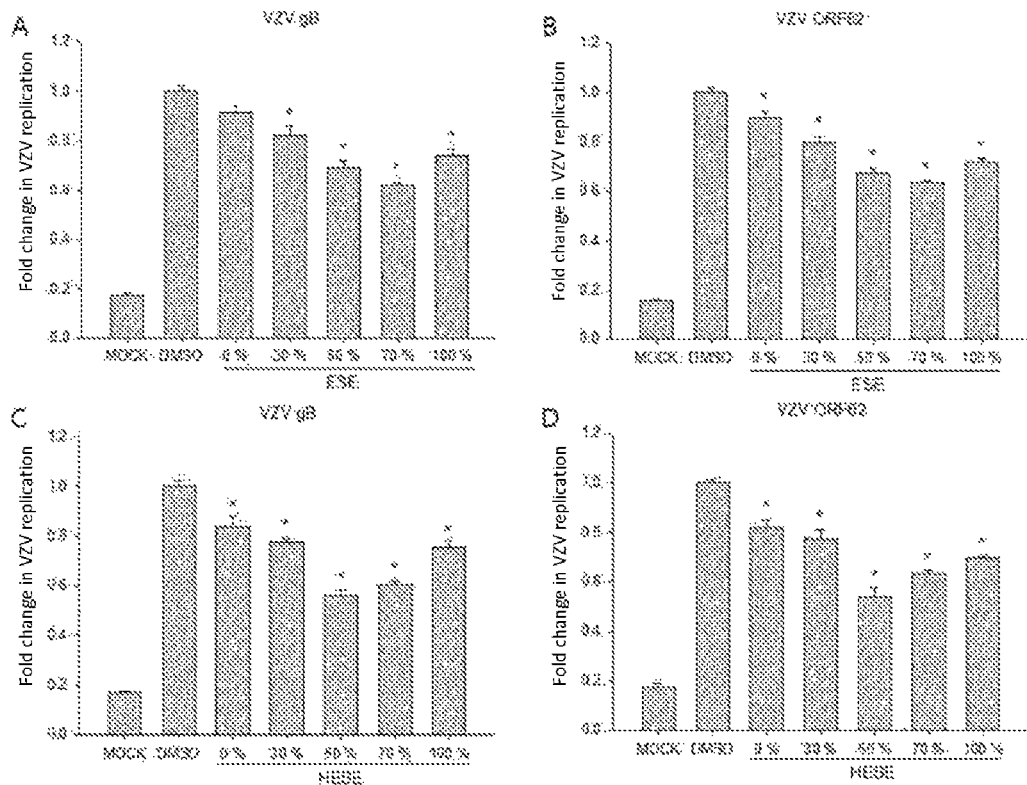
FIG. 9 shows the inhibitory effects of an *Elaeocarpus sylvestris* extract (ESE) and heated *Elaeocarpus sylvestris* extract (HESE) of the present invention on the expression of VZV replication-related genes. Specifically, (A) shows the expression level of VZV glycoprotein B gene when treated with the *Elaeocarpus sylvestris* extract; (B) shows the expression level of VZV open reading frame 62 gene when treated with the *Elaeocarpus sylvestris* extract; (C) shows the expression level of VZV gB gene when treated with the heated *Elaeocarpus sylvestris* extract; and (D) shows the expression level of VZV ORF62 gene when treated with the heated *Elaeocarpus sylvestris* extract (* $P<0.05$).
Figure 10:
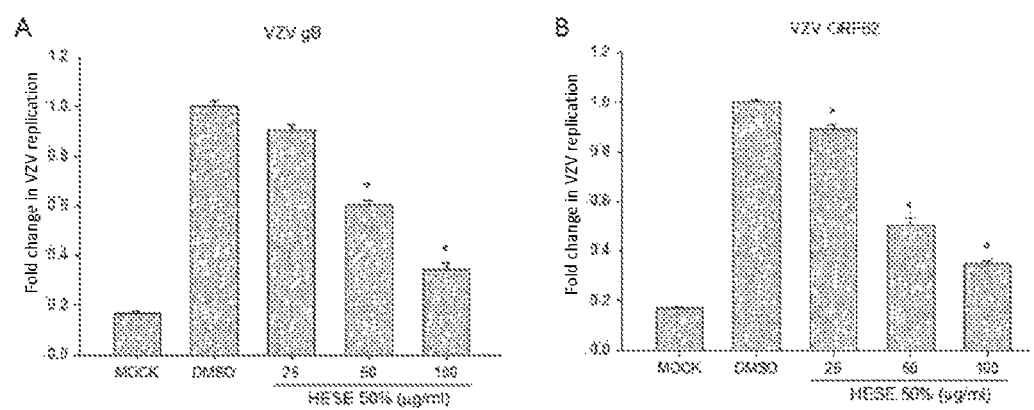
FIG. 10 shows the inhibitory effects of a heated *Elaeocarpus sylvestris* extract of the present invention on the expression of VZV replication-related genes. Specifically, (A) shows the expression level of VZV gB gene when treated with a 50% ethanol heated *Elaeocarpus sylvestris* extract, and (B) shows the expression level of VZV ORF62 gene when treated with a 50% ethanol heated *Elaeocarpus sylvestris* extract (* $P<0.05$).
Figure 11:
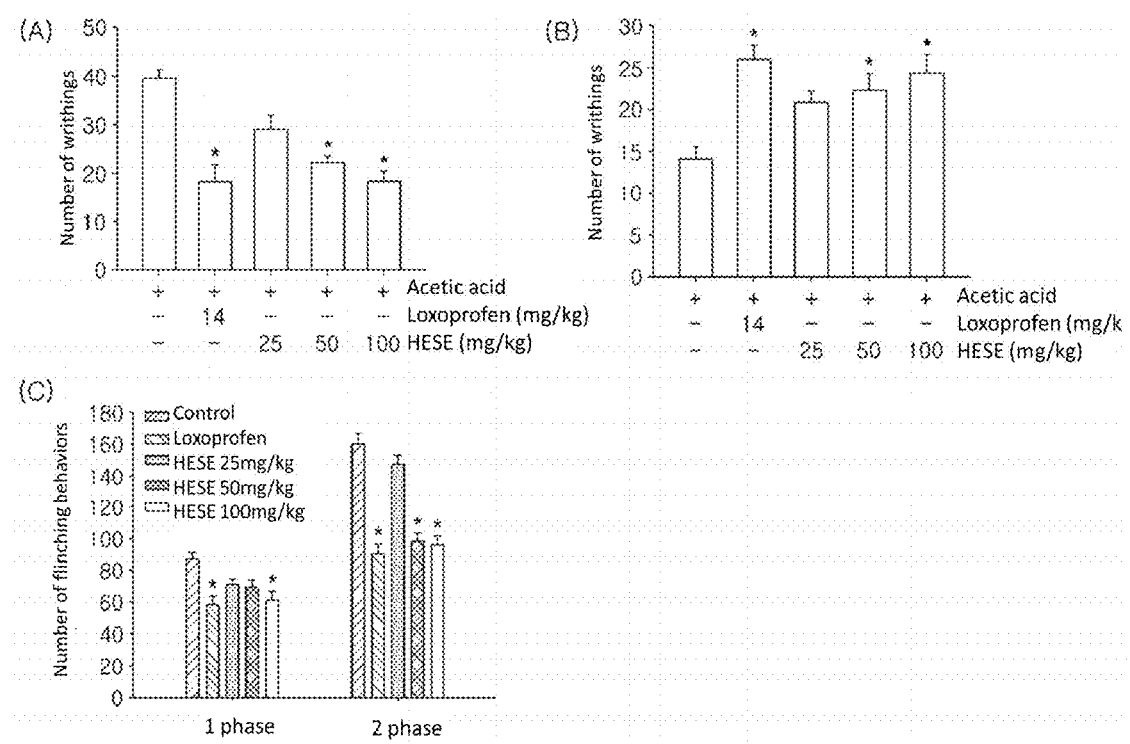
FIG. 11 shows the pain inhibitory effect of a heated *Elaeocarpus sylvestris* extract in mice. Specifically, (A) shows the analgesic effect of the heated *Elaeocarpus sylvestris* extract after oral administration in an acetic acid-induced writhing test; (B) shows the central pain inhibitory effect of the heated *Elaeocarpus sylvestris* extract after oral administration in a hot plate test; and (C) shows the pain inhibitory effect of the heated *Elaeocarpus sylvestris* extract after oral administration against inflammatory pain induced by formalin injection (* $P<0.05$).
Figure 12:
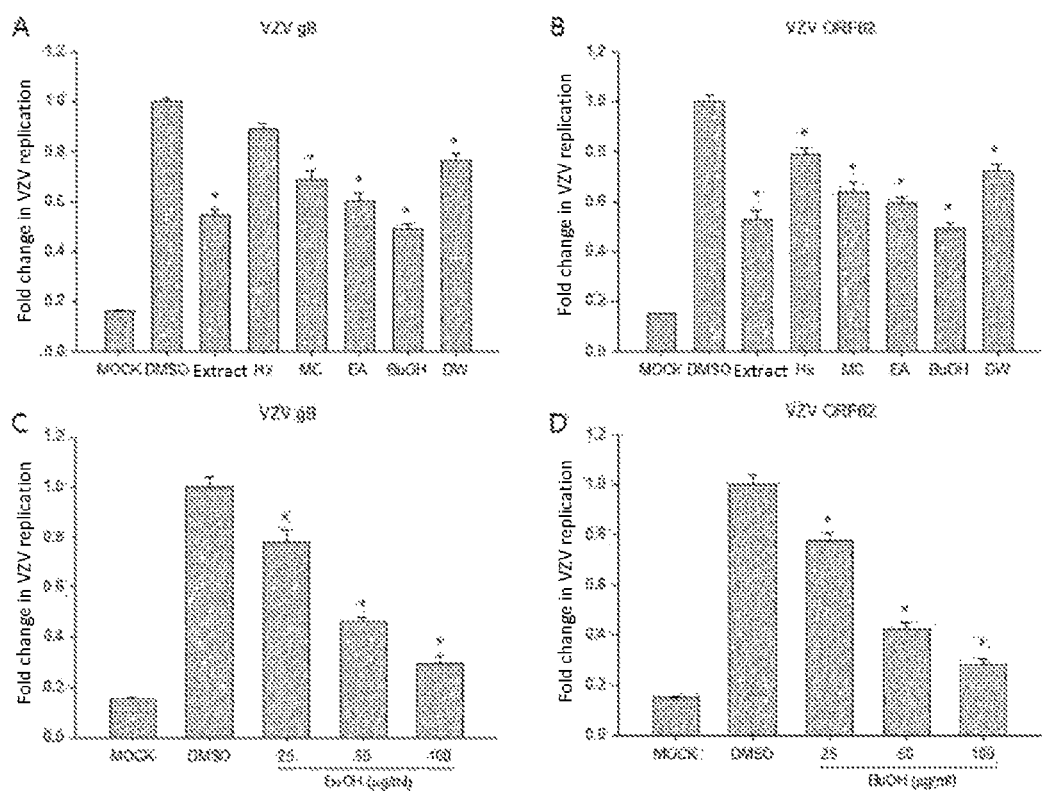
FIG. 12 shows the inhibitory effects of an *Elaeocarpus sylvestris* extract and its fractions (Hx, MC, EA, BuOH and DW) of the present invention on VZV replication. Specifically, (A) shows the expression level of VZV glycoprotein B gene when treated with the *Elaeocarpus sylvestris* extract and its fractions (Hx, MC, EA, BuOH and DW); (B) shows the expression level of VZV open reading frame 62 gene when treated with the *Elaeocarpus sylvestris* extract and its fractions (Hx, MC, EA, BuOH and DW); (C) shows the expression level of VZV gB gene when treated with the *Elaeocarpus sylvestris* extract and its fractions (Hx, MC, EA, BuOH and DW); and (D) shows the expression level of VZV ORF62 gene when treated with a butanol fraction of the *Elaeocarpus sylvestris* extract (* $P<0.05$).

After treatment with various concentrations of the 50% ethanol heated extract of *Elaeocarpus sylvestris*, which had the best inhibitory effect on the replication of HSV-1 and HSV-2, the expression levels of gD and ICP0 were measured, and the results are shown in FIG. 8. As shown in FIG. 8, the 50% ethanol heated extract of *Elaeocarpus sylvestris* showed a concentration-dependent inhibitory effect on the replication of HSV-1/2.

Example 3: Test for Evaluation of the Inhibitory Effect of *Elaeocarpus sylvestris* Extract on Expression of VZV Replication-Related Genes The inhibitory effect of the *Elaeocarpus sylvestris* extract against varicella-zoster virus (VZV) belonging to alpha-herpesviruses was analyzed.

MRC-5 cells, which are human fetal lung fibroblasts capable of being infected with VZV, were infected with VZV by culturing them with VZV-infected cells at a cell-to-cell ratio of 1:8, and then treated with various ethanol extracts of *Elaeocarpus sylvestris* and various heated ethanol extracts of *Elaeocarpus sylvestris* (50 µg/mL). Next, on 3 days after the infection, the cells were collected, and the inhibitory effect on viral replication was analyzed by real-time PCR using VZV glycoprotein B (gB) and open reading frame 62 (ORF62) DNAs.

The results are shown in FIG. 9.

As shown in FIG. 9, among the *Elaeocarpus sylvestris* extracts, the 70% ethanol extract (37.76%) showed the best inhibitory effect on viral replication, and among the heated extracts, the 50% ethanol heated extract (44.14%) showed the best inhibitory effect on viral replication. When the extracts were compared with the heated extracts, the heated extracts showed better inhibitor effects on the replication of VZV virus than the extracts obtained at room temperature.

After treatment with various concentrations of the 50% ethanol heated extract of *Elaeocarpus sylvestris*, had the best inhibitory effect on viral replication, the expression levels of gB and ORF62 were measured, and the results are shown in FIG. 10. As shown in FIG. 10, the 50% ethanol heated extract of *Elaeocarpus sylvestris* showed a concentration-dependent inhibitory effect on the replication of VZV.

Example 4: Pain Inhibitory Effect of *Elaeocarpus sylvestris* Extract

Infection with alpha-herpesvirus causes herpes. In particular, when it causes herpes zoster, the pain is very severe. Thus, the effect of the *Elaeocarpus sylvestris* extract of the present invention against peripheral and central inflammatory pain was evaluated.

As experimental animals, 5-week-old ICR mice (Central Laboratory Animals, Seoul, Korea) were purchased, acclimated in an animal care facility for 1 week at a humidity of 50% and a temperature of 24 to 26° C., and allowed to access feed and water ad libitum.

(A) To evaluate the inhibitory effect against peripheral pain, an acetic acid-induced writhing test, which is based on abdominal contraction response and is mainly used to test the analgesic effect of drugs against peripheral pain, was performed. An irritant (saline containing 0.75% acetic acid) was injected at a dose of 0.1 mL/10 g body weight into the abdominal cavity of mice fasted for 12 hours before the experiment, and the heated extract of *Elaeocarpus sylvestris* was administered orally to the mice at 60 minutes before injection of the irritant. Administration of the irritant induces pain in the abdominal cavity, and the mice show writhing syndrome such as contortion, twisting the hind leg inward, or stretching. The number of writhings was counted for a total of 10 minutes.

(B) To evaluate the inhibitory effect against central pain, a hot plate test, a method used to search for analgesic agents acting on the central nervous system, was performed. Rats are very sensitive to heat in the sole of the paws, so if the rats feel unbearable heat, they jump, or shake or lick the paws. Thus, the hot plate test is a method of measuring the time from when a rat comes into contact with a hot plate to when it shakes or licks the hind paw. At 60 minutes after the heated extract of *Elaeocarpus sylvestris* was administered orally, the time from when the test starts to the time when the rat shakes or licks the hind paw was measured in seconds.

(C) To evaluate the inhibitory effect against inflammatory pain, formalin was injected into white rats, and the number of flinching behaviors was measured. At 1 hour before formalin was injected, the heated extract of *Elaeocarpus sylvestris* was administered orally to the rats at doses of 25, 50 and 100 mg/kg. 50 μL of 5% formalin was injected subcutaneously into one hind paw of white rats, and then the rats were placed in an observation chamber, and the number of flinching behaviors, such as biting or licking the paws, was measured at 0 to 12 minutes (phase 1) and 24 to 39 minutes (phase 2).

The results are shown in FIG. 11.

As shown in FIG. 11(A), the *Elaeocarpus sylvestris* extract exhibited a dose-dependent pain inhibitory effect in the acetic acid-induced writhing test, and as shown in FIG. 11(B), the *Elaeocarpus sylvestris* extract showed a dose-dependent decrease in the number of writhings, indicating that the extract exhibited an inhibitory effect against central pain. In addition, as shown in FIG. 11(C), in phase 1 that is pain caused by formalin injection (noxious stimulus), the number of flinching behaviors in the group administered with the heated extract of *Elaeocarpus sylvestris* greatly decreased compared to that in the control group. In phase 2 that is pathological pain caused by peripheral sensitization in peripheral tissue, which is promoted by phase 1 and formed by a continually maintained stimulus, and central sensitization in the spinal cord olfactory, the number of flinching behaviors in the group administered with the heated extract of *Elaeocarpus sylvestris* greatly decreased compared to that in the control group.

Example 5: Test for Evaluation of the Inhibitory Effect of Fraction of *Elaeocarpus sylvestris* Extract on Expression of VZV Replication-Related Genes MRC-5 cells were infected with VZV by culturing them with VZV-infected cells at a cell-to-cell ratio of 1:8, and treated with the *Elaeocarpus sylvestris* extract and its fractions (extract, hexane (Hx), dichloromethane (MC), ethyl acetate (EA), butanol (BuOH), and distilled water (DW) 50 μg/mL). On 3 days after the infection, the cells were collected, and the inhibitory effect against viral replication was analyzed by real-time PCR using VZV glycoprotein B (gB) and open reading frame 62 (ORF62) DNAs.

The results are shown in FIG. 12. As shown in FIG. 12(A), the BuOH layer showed the best inhibitory effect against the replication of VZV. Furthermore, as shown in FIGS. 12(B) and 12(C), after treatment with various concentrations of the BuOH layer showing the best inhibitory effect against viral replication, the expression levels of gB and ORF62 were measured, and as a result, the BuOH layer showed a concentration-dependent inhibitory effect against viral replication. In addition, as shown in FIG. 12(D), the BuOH fraction showed an excellent concentration-dependent effect on the inhibition of VZV.

Example 6: HSV Replication Inhibition Test in Animal Models

BALB/c nude mice, typical athymic mice, are animals that are frequently used in the field of tumor studies and immunogenetics due to lack of the lymphoid organ thymus. These mice produce monoclonal antibodies, and thus are suitable for virus-associated disease models. Thus, HSV-infected mouse models were used to measure the survival rate of mice and the inhibition of viral proliferation.

BALB/c nude mice as experimental animals were purchased from RaonBio Co., Ltd. (Korea), divided into groups, acclimated for 1 week, and then infected with 5.75×10⁷ PEU of HSV. Each of the 50% ethanol heated extract of *Elaeocarpus sylvestris* and Acyclovir was orally administered once a day to the mice for 10 days, and infection was observed daily. On 30 days after the infection, the survived mice were biopsied, and the mRNA level of ICP0 in the lung tissue was measured by real-time PCR, thereby evaluating the virus inhibitory effect of the extract.

TABLE 6

| No. | Test groups | Drugs administered (p.o.) |
| --- | --- | --- |
| 1 | Normal group | Saline |
| 2 | Control group | Saline |
| 3 | Positive control group | Acyclovir (ACV), 25 mg/kg (i.p.) |
| 4 | Group administered with low dose of *Elaeocarpus sylvestris* extract | *Elaeocarpus sylvestris* extract, 25 mg/kg |
| 5 | Group administered with middle dose of *Elaeocarpus sylvestris* extract | *Elaeocarpus sylvestris* extract, 50 mg/kg |
| 6 | Group administered with high dose of *Elaeocarpus sylvestris* extract | *Elaeocarpus sylvestris* extract, 100 mg/kg |

Figure 13:
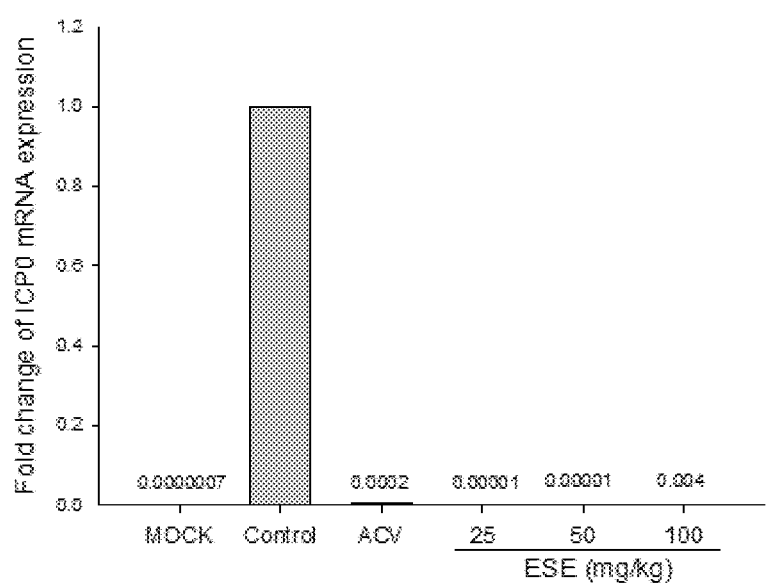
FIG. 13 shows that an *Elaeocarpus sylvestris* extract of the present invention inhibits gene expression by inhibiting the replication of HSV in animal models.

The results are shown in FIG. 13. As shown in FIG. 13, it was confirmed that the 50% ethanol heated extract of *Elaeocarpus sylvestris* inhibited ICP0, similar to the positive control Acyclovir.

Example 7: VZV Replication Inhibition Test in Animal Models

VZV-infected mouse models were used to measure the survival rate of mice and the inhibition of viral proliferation. BALB/c nude mice as experimental animals were purchased from RaonBio Co., Ltd. (Korea), divided into groups, and acclimated for 1 week, and then VZV-infected cells were injected into the skin of the mice. Each of the 50% ethanol heated extract of *Elaeocarpus sylvestris* and Acyclovir was orally administered once a day to the mice for 10 days, and infection was observed daily. On days 14 and 21, the skin was dissected, and RNA was extracted therefrom and analyzed by real-time PCR using VZV glycoprotein B (gB) and open reading frame 62 (ORF62) DNAs. The results are shown in FIG. 14.

TABLE 7

| No. | Test groups | Drugs administered (p.o.) |
| --- | --- | --- |
| 1 | Normal group | Saline |
| 2 | Control group | Saline |
| 3 | Positive control group | Acyclovir (ACV), 25 mg/kg (i.p.) |
| 4 | Group administered with low dose of *Elaeocarpus sylvestris* extract | *Elaeocarpus sylvestris* extract, 25 mg/kg |
| 5 | Group administered with middle dose of *Elaeocarpus sylvestris* extract | *Elaeocarpus sylvestris* extract, 50 mg/kg |
| 6 | Group administered with high dose of *Elaeocarpus sylvestris*extract | *Elaeocarpus sylvestris* extract, 100 mg/kg |

Figure 14:
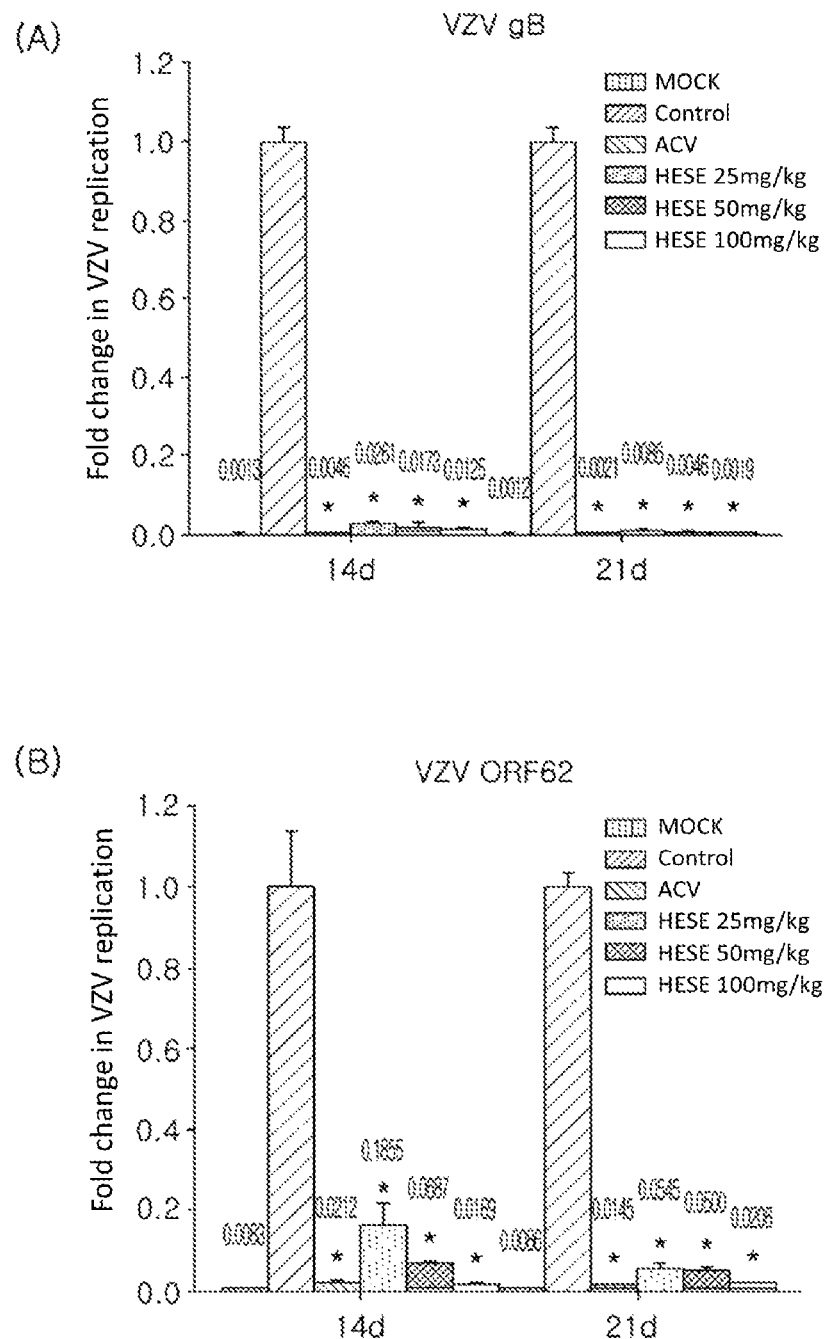
FIG. 14 shows the inhibitory effect of an *Elaeocarpus sylvestris* extract of the present invention on the expression of VZV replication-related genes in animal models. Specifically, (A) shows the expression level of VZV glycoprotein B gene when treated with the *Elaeocarpus sylvestris* extract, and (B) shows the expression level of VZV open reading frame 62 gene when treated with the *Elaeocarpus sylvestris* extract (* $P<0.05$).

As shown in FIG. 14, treatment with the *Elaeocarpus sylvestris* extract showed dose-dependent decreases in VZV glycoprotein B (gB) and open reading frame 62 (ORF62), and these decreases were similar to the levels shown in the positive control group.

Example 8: Evaluation of Autophagic Activity of *Elaeocarpus sylvestris* Extract When autophagy activation in virus-infected host cells is promoted, autophagosomes that cause autophagy can be produced and can degrade the virus. Thus, in order to examine whether the *Elaeocarpus sylvestris* extract of the present invention can further promote autophagy activation in a process in which VZV-infected cells cause autophagy activation to inhibit VZV by themselves, an experiment was performed.

Figure 15:
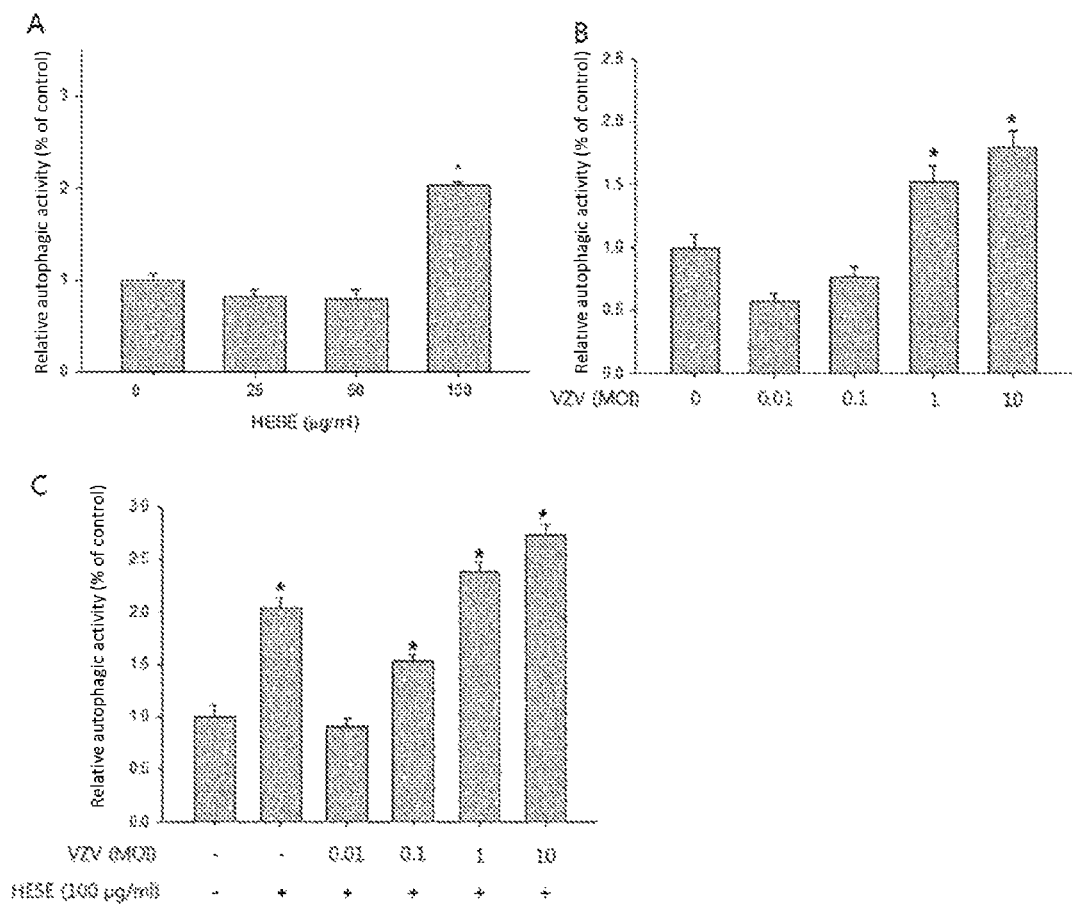
FIG. 15 shows the autophagic activity of an *Elaeocarpus sylvestris* extract of the present invention. Specifically, (A) shows autophagic activity after the mouse normal liver cell line MRC-5 was treated with a 50% ethanol heated *Elaeocarpus sylvestris* extract; (B) shows autophagic activity upon infection with various concentrations of VZV; and (C) shows autophagic activity after VZV-infected cells were treated with a heated *Elaeocarpus sylvestris* extract.

In order to measure the autophagic activity of the 50% ethanol heated extract of *Elaeocarpus sylvestris*, MRC-5 cells which are mouse normal liver cells were treated with the 50% ethanol heated extract of *Elaeocarpus sylvestris*, and the autophagic activity of the extract was evaluated using Cyto-ID® Autophagy Detection Kit (Enzo®, ENZ-51031). The results are shown in FIG. 15. As shown in FIG. 15A, the autophagic activity of the 50% ethanol heated extract of *Elaeocarpus sylvestris* increased about 2-fold compared to the control.

In order to examine autophagic activity when infected with VZV, MRC-5 cells were infected with 0.01, 0.1, 1 and 10 MOI of VZV, and then autophagic activity in the cells was evaluated using Cyto-ID® Autophagy Detection Kit (Enzo®, ENZ-51031). As a result, as shown in FIG. 15B, when the amount of VZV was small, the autophagic activity did not increased, but when infected with 1 MOI of VZV, the autophagic activity increased about 1.5-fold compared to the control, and when infected with 10 MOI of VZV, the autophagic activity increased about 1.7-fold.

Next, in order to examine the effect of the heated extract of *Elaeocarpus sylvestris* against VZV-infected cells, MRC-5 cells were infected with 0.01, 0.1, 1 and 10 MOI of VZV, and then treated with 100 µg/mL of the 50% ethanol heated extract of *Elaeocarpus sylvestris*, after which the autophagic activity of the extract activity was evaluated Cyto-ID® Autophagy Detection Kit (Enzo®, ENZ-51031). As a result, as shown in FIG. 15C, when infected with VZV alone, no autophagic activity appeared at low concentration, but when treated with the 50% ethanol heated extract of *Elaeocarpus sylvestris*, the autophagic activity increased 1.65-fold compared to the control at 0.1 MOI and increased 2.58-fold at 1 MOI. Thus, it was confirmed that when the cells were infected with VZV, treatment of the cells with the extract of *Elaeocarpus sylvestris* increased the autophagic activity, and thus VZV could be degraded in the cells.

Example 9: Test for Evaluation of the Inhibitory Effect of *Elaeocarpus sylvestris* Extract Components on Expression of VZV Replication-Related Genes In order to analyze the VZV replication inhibitory effect and target of *Elaeocarpus sylvestris* extract components, MRC-5 cells were infected with VZV by culturing them with VZV-infected cells at a cell-to-cell ratio of 1:8, and treated with 50 µg/mL of each of *Elaeocarpus sylvestris* extract fractions (DS-1, DS-2, DS-3 and DS-4). On 3 days after the infection, the cells were collected, and the viral replication inhibitory effect of the fractions was analyzed by real-time PCR using VZV glycoprotein B (gB) and open reading frame 62 (ORF62) DNAs.

Figure 16:
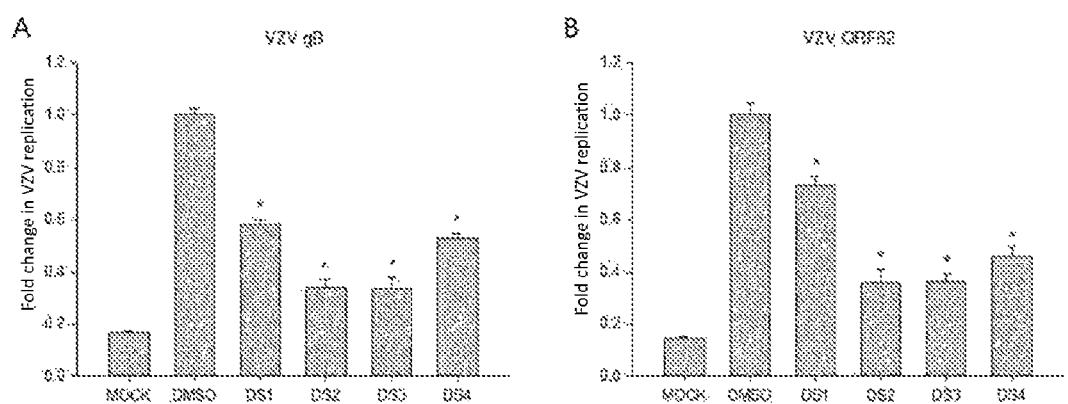
FIG. 16 shows the VZV replication inhibitory effects of components (DS-1, DS-2, DS-3 and DS-4) separated from an *Elaeocarpus sylvestris* extract of the present invention on VZV replication. Specifically, (A) shows the expression level of VZV glycoprotein B gene when treated with the separated components, and (B) shows the expression level of VZV open reading frame 62 when treated with the separated components (* $P<0.05$).

The results are shown in FIG. 16. As a result, as shown in FIG. 16, it was confirmed that the expressions of VZV glycoprotein B (gB) and open reading frame 62 (ORF62)

were decreased by treatment with each of the *Elaeocarpus sylvestris* extract fractions (DS-1, DS-2, DS-3 and DS-4).

Formulation Example 1: Preparation of Tablet for Oral Administration Containing *Elaeocarpus sylvestris* Extract The *Elaeocarpus sylvestris* extract was mixed with an excipient for 15 minutes, and then finally mixed with a lubricant. The final mixture was used as a reference mass and compressed into a tablet by means of a tableting machine. The uncoated tablet was primarily coated using hypromellose as a coating agent, and the primarily coated material was secondarily coated using polyvinyl alcohol as a coating agent, thereby producing a tablet for oral administration containing the *Elaeocarpus sylvestris* extract.

The invention claimed is:

1. A method for treating alpha-herpes virus infection comprising administering a pharmaceutical composition comprising an *Elaeocarpus sylvestris* extract or a fraction thereof to a subject in need thereof, wherein the *Elaeocarpus sylvestris* extract is an ethanol extract.

2. The method of claim 1, wherein the *Elaeocarpus sylvestris* extract is a 50% ethanol extract.

3. The method of claim 1, wherein the alpha-herpes virus is selected from the group consisting of varicella-zoster virus (VZV), herpes simplex virus-1 (HSV-1), herpes simplex virus-2 (HSV-2) and mixtures thereof.

4. The method of claim 1, wherein the *Elaeocarpus sylvestris* extract is heated *Elaeocarpus sylvestris* extract, wherein the heated *Elaeocarpus sylvestris* extract is obtained by heat extraction at 70° C. to 80° C.

5. The method of claim 1, wherein the alpha-herpes virus infection is selected from the group consisting of herpes, genital herpes, chickenpox, herpes zoster and mixtures thereof.

6. The method of claim 1, wherein the *Elaeocarpus sylvestris* extract comprises a compound selected from the group consisting of methyl gallate, geraniin, casuarictin and mixtures thereof.

* * * * *